US007136694B2

(12) United States Patent
Hadley et al.

(10) Patent No.: US 7,136,694 B2
(45) Date of Patent: *Nov. 14, 2006

(54) METHODS FOR QUANTIFYING THE MORPHOLOGY AND AMPLITUDE OF CARDIAC ACTION POTENTIAL ALTERNANS

(75) Inventors: David Milton Hadley, Woodinville, WA (US); Mustafa Hikmet Sagiroglu, Bellevue, WA (US)

(73) Assignee: Cardiac Science Corporation, Bothell, WA (US)

( * ) Notice: Subject to any disclaimer, the term of this patent is extended or adjusted under 35 U.S.C. 154(b) by 50 days.

This patent is subject to a terminal disclaimer.

(21) Appl. No.: 10/815,290

(22) Filed: Mar. 30, 2004

(65) Prior Publication Data

US 2005/0222510 A1 Oct. 6, 2005

(51) Int. Cl.
*A61B 5/04* (2006.01)

(52) U.S. Cl. .................................... 600/515; 600/509

(58) Field of Classification Search ........ 600/515–517, 600/522, 523, 508
See application file for complete search history.

(56) References Cited

U.S. PATENT DOCUMENTS

| | | | |
|---|---|---|---|
| 4,732,157 A | 3/1988 | Kaplan et al. | |
| 4,802,491 A | 2/1989 | Cohen et al. | |
| 5,148,812 A * | 9/1992 | Verrier et al. | 600/517 |
| 5,265,617 A | 11/1993 | Verrier et al. | |
| 5,318,036 A | 6/1994 | Arand et al. | |
| 5,437,285 A | 8/1995 | Verrier et al. | |
| 5,555,888 A | 9/1996 | Brewer et al. | |
| 5,570,696 A | 11/1996 | Arnold et al. | |
| 5,704,365 A | 1/1998 | Albrecht et al. | |
| 5,713,367 A * | 2/1998 | Arnold et al. | 600/517 |
| 5,792,065 A | 8/1998 | Xue et al. | |
| 5,803,084 A * | 9/1998 | Olson | 600/512 |
| 5,827,195 A | 10/1998 | Lander | |
| 5,842,997 A | 12/1998 | Verrier et al. | |
| 5,921,940 A | 7/1999 | Verrier et al. | |
| 5,935,082 A | 8/1999 | Albrecht et al. | |
| 6,169,919 B1 | 1/2001 | Nearing et al. | |
| 6,370,423 B1 * | 4/2002 | Guerrero et al. | 600/513 |
| 6,409,659 B1 * | 6/2002 | Warner et al. | 600/300 |
| 6,453,191 B1 | 9/2002 | Krishnamachari | |
| 6,741,887 B1 * | 5/2004 | Gleeson | 600/523 |
| 6,778,852 B1 * | 8/2004 | Galen et al. | 600/523 |
| 2003/0060724 A1 | 3/2003 | Thiagarajan et al. | |
| 2003/0069512 A1 | 4/2003 | Kaiser et al. | |
| 2005/0010122 A1 | 1/2005 | Nearing et al. | |

OTHER PUBLICATIONS

Ackerman, et al., "Ion Channels—Basic Science and Clinical Disease," New England Journal of Medicine, vol. 336 (22), pp. 1575-1586, 1977.

Adam, et al., "Estimation of Ventricular Vulnerability to Fibrillation Through T-Wave Time Series Analysis," Computers in Cardiology, pp. 307-310, Sep. 1981.

(Continued)

*Primary Examiner*—Robert E. Pezzuto
*Assistant Examiner*—Brian T. Gedeon
(74) *Attorney, Agent, or Firm*—Perkins Coie LLP

(57) ABSTRACT

Methods and apparatus for determining T-wave alternan signatures (i.e., morphology and polarity) derived from a physiologic signal representative of a subject's heart activity; assessing changes in the myocardium Action Potential ("AP") through analysis of the alternan signature derived from a physiologic signal representative of a subject's heart activity; and/or assessing spatial disassociation of alternan characteristics that are likely associated with the initiation of re-entrant arrhythmias.

27 Claims, 20 Drawing Sheets

OTHER PUBLICATIONS

Adam, et al., "Fluctuations in T-Wave Morphology and Susceptibility to Ventricular Fibrillation," Journal of Electrocardiology, vol. 17(3), pp. 209-218, 1984.

Adam, et al., "Ventricular Fibrillation and Fluctuations in the Magnitude of the Repolarization Vector," Computers in Cardiology, pp. 241-244, 1982.

Carson, et al., "Characterisation of unipolar waveform alternation in acutely ischaemic porcine myocardium," Cardiovascular Research, vol. 20, pp. 521-527, 1986.

Chinushi, et al., "Electrophysiological Basis of Arrhythmogenicity of QT/T Alternans in the Long-QT Syndrome—Tridimensional Analysis of the Kinetics of Cardiac Repolarization," Circulation Research, vol. 83 (6), pp. 614-628, Sep. 21, 1998.

Cinca, et al., "Mechanism and Time Course of the Early Electrical Changes During Acute Coronary Artery Occlusion—An Attempt to Correlate the Early ECG Changes in Man to the Cellular Electrophysiology in the Pig," Chest, vol. 77, pp. 499-505, Apr. 1980.

Coetzee, et al., "Effects of thiol-modifying agents on $K_{ATP}$ channels in guinea pig ventricular cells," American Journal of Physiology, vol. 38, pp. H1625-H1633, 1995.

Coronel, et al., "Reperfusion arrhythmias in isolated perfused pig hearts—Inhomogeneities in extracellular potassium, ST and TQ potentials, and transmembrane action potentials," Circulation Research, vol. 71 (5), pp. 1131-1142, Nov. 1992.

Demidowich, et al., "Electrical alternans of the ST segment in non-Prinzmetal's angina," PACE, vol. 3, pp. 733-736, Nov.-Dec. 1980.

Di Bernardo, et al., "Effect of changes in heart rate and in action potential duration on the electrocardiogram T wave shape," Abstract only, Physiol Meas, vol. 23 (2), pp. 355-364, May 2002.

Duckett, et al., "Modeling the Dynamics of Cardiac Action Potentials," Physical Review Letters, vol. 84 (4), pp. 884-887, Jul. 24, 2000.

Gima, et al., "Ionic Current Basis of Electrocardiographic Waveforms—A Model Study," Circulation Research, vol. 90, pp. 889-896, May 2002.

Han, "Ventricular vulnerability during acute coronary occlusion," American Journal of Cardiology, vol. 24, pp. 857-864, Dec. 1969.

Han, et al., "Temporal dispersion of recovery of excitability in atrium and ventricle as a function of heart rate," American Heart Journal, vol. 71 (4), pp. 481-487, Apr. 1966.

Hashimoto, et al., "Effects of calcium antagonists on the electrical alternans of the ST segment and on associated mechanical alternans during acute coronary occlusion in dogs," Circulation, vol. 68 (3): 667-672, Sep. 1983.

Hashimoto, et al., "Effects of the ventricular premature beat on the alternation of the repolarization phase in ischemic myocardium during acute coronary occlusion in dogs," Abstract only, Journal of Electrocardiology, vol. 17 (3), pp. 229-238, Jul. 1984.

Hellerstein, et al., "Electrical alternation in experimental coronary artery occlusion," American Journal of Physiology, vol. 160, pp. 366-374, Feb. 1950.

Kass, et al., "Channel structure and drug-induced cardiac arrhythmias," PNAS, vol. 97 (22), pp. 11683-11684, Oct. 24, 2000.

Kažić et al., "Ion Channels and Drug Development—Focus on Potassium Channels and Their Modulators," Medicine and Biology, vol. 6 (1), pp. 23-30, 1999.

Kleinfeld, et al., "Alternans of the ST Segment in Prinzmetal's Angina," Circulation, vol. 55 (4), pp. 574-577, Apr. 1977.

Kleinfeld, et al., "Electrical alternans of components of action potential," American Heart Journal, vol. 75 (4), pp. 528-530, Apr. 1968.

Konta, et al., "Significance of discordant ST alternans in ventricular fibrillation," Circulation, vol. 82 (6), pp. 2185-2189, Dec. 1990.

Kubota, et al., "Role of ATP-Sensitive $K^+$ Channel of ECG ST Segment During a Bout of Myocardial Ischemia—A Study of Epicardial Mapping in Dogs," Circulation, vol. 88 (4, Part 1), pp. 1845-1851, Oct. 1993.

Kurz, et al., "Ischaemia induced alternans of action potential duration in the intact-heart: dependence on coronary flow, preload and cycle length," European Heart Journal, vol. 14, pp. 1410-1420, 1993.

Lukas, et al., "Differences in the electrophysiological response of canine ventricular epicardium and endocardium to ischemia: Role of the transient outward current," Circulation, vol. 88 (6), pp. 2903-2915, Dec. 1993.

Moody, et al., "Clinical Validation of the ECG-Derived Respiration (EDR) Technique," Computers in Cardiology, pp. 507-510, 1986.

Nakashima, et al., "Experimental studies and clinical report on the electrical alternans of ST segment during myocardial ischemia," Japanese Heart Journal, vol. 19 (3) pp. 396-408, May 1978.

Nearing, et al., "Dynamic Tracking of Cardiac Vulnerability by Complex Demodulation of the T Wave," Science, vol. 252, pp. 437-440, Apr. 1991.

Nearing, et al., "Modified moving average analysis of T-wave alternans to predict ventricular fibrillation with high accuracy," Journal of Applied Physiology, vol. 92, pp. 541-549, Feb. 2002.

Nearing, et al., "Tracking States of Heightened Cardiac Electrical Instability by Computing Interlead Heterogeneity of T-Wave Morphology Using Second Central Moment Analysis," J Appl Physiol, vol. 95, pp. 2265-2272, Dec. 2003., 41 pages (First published Aug. 1, 2003; 10.1152/japplphysiol.00623.2003).

Pastore, et al., "Mechanism Linking T-Wave Alternans to the Genesis of Cardiac Fibrillation," Circulation, vol. 99, pp. 1385-1394, Mar. 1999.

Raeder, et al., "Alternating Morphology of the QRST Complex Preceding Sudden Death," New England Journal of Medicine, vol. 326 (4), pp. 271-272, Jan. 23, 1992.

Ring, et al., "Exercise-Induced ST Segment Alternans," American Heart Journal, vol. 111 (5), pp. 1009-1011, May 1986.

Roden, et al., "Cardiac Ion Channels," Annual Review Physiology, vol. 64, pp. 431-475, 2002.

Salerno, et al., "Ventricular arrhythmias during acute myocardial ischaemia in man. The role and significance of R-ST-T alternans and the prevention of ischaemic sudden death by medical treatment," European Heart Journal, vol. 7 Suppl A, pp. 63-75, 1986.

Schram, et al., "Differential Distribution of Cardiac Ion Channel Expression as a Basis for Regional Specialization in Electrical Function," Circulation Research, vol. 90, pp. 939-950, May 2002.

Smith, et al., "Electrical Alternans and Cardiac Electrical Instability," Circulation, vol. 77 (1), pp. 110-121, Jan. 1988.

Smith, et al., "Subtle Alternating Electrocardiographic Morphology as an Indicator of Decreased Cardiac Electrical Stability," Computers in Cardiology, pp. 109-112, 1985.

Verrier, et al., "Risk Identification by Noninvasive Markers of Cardiac Vulnerability," Foundations of Cardiac Arrhythmias-Basic Concepts and Clinical Approaches, P. Spooner and M. Rosen (eds.), Marcel Dekker, Inc., pp. 745-777, 2000.

Verrier, et al., "Electrophysiologic Basis for T Wave Alternans as an Index of Vulnerability to Ventricular Fibrillation," Journal of Cardiovascular Electrophysiology, vol. 5, pp. 445-461, May 1994.

Walker, et al., "Repolarization alternans: implications for the mechanism and prevention of sudden cardiac death," Abstract only, Cardiovascular Research, vol. 57 (3), pp. 599-614, Mar. 2003.

Wayne, et al., "Exercise-induced ST segment alternans," Chest, vol. 83 (5), pp. 824-825, May 1983.

* cited by examiner

METHODS FOR QUANTIFYING THE MORPHOLOGY AND AMPLITUDE OF CARDIAC ACTION POTENTIAL ALTERNANS

TECHNICAL FIELD

The present invention relates to methods and apparatus for determining T-wave alternan signatures (i.e., morphology and polarity) derived from a physiologic signal representative of a subject's heart activity; assessing changes in the myocardium Action Potential ("AP") through analysis of the alternan signature derived from a physiologic signal representative of a subject's heart activity; and/or assessing spatial disassociation of alternan characteristics that are likely associated with the initiation of re-entrant arrhythmias.

BACKGROUND

T-wave alternans are characterized by a pattern of alternations in the amplitude of the T-wave component of an ECG, where the even beats systematically display a different amplitude than the odd beats (an "ABABAB . . . " pattern of beat signatures). Many prior research efforts have found correlations between the amplitude of the T-wave alternans during periods of increased heart rates, and sudden cardiac arrest or arrhythmias. Verrier and Cohen, in their chapter "Risk Identification by Noninvasive Markers of Cardiac Vulnerability" (Foundations of Cardiac Arrhythmias, Spooner and Rosen editors, Marcel Dekker, Inc., 2000), provide an overview of past research and describe a signal processing method for determining the presence of microvolt level alternans. Summarily stated, the ECG signal is evaluated to identify sequential data points within the T-waves. The amplitude of these selected points, from successive beats, forms pseudo time series that are next subjected to Fourier analysis to create a power spectrum; the power at the Nyquist frequency of this spectrum provides an estimate of the energy of the beat-to-beat fluctuations in the amplitude of the T-wave. The power spectra from successive individual spectra associated with different offset times within the T-wave coda are averaged to establish a composite power spectra, which is claimed to be useful in assessing patient risk for sudden cardiac arrest or arrhythmias. Clinical observations and trials have shown that persons who exhibit T-wave alternans at relatively low heart rates, i.e., ~110 bpm, are at greater risk of developing fatal arrhythmias than those who exhibit alternans at heart rates approaching their maximum target heart rate. Both this publication, as well as U.S. Pat. Nos. 4,802,491; 5,148,812; and 5,713,367 relating to this and related approaches are incorporated herein by reference.

While the above-described method may be valuable for establishing the gross existence and severity of T-wave alternans, the analysis is limited to only the average amplitude of the alternan signal across the entire T-wave signal. Clinical experience with stratifying patient risk of sudden cardiac death based upon this simplistic characterization of the alternan signal are typified by a high rate of indeterminacy—typically as high as 30% of the patient tests for alternans are indeterminate.

SUMMARY

The invention is broadly directed to cardiac assessments derived through T-wave analysis. Additional information contained within the alternan signal may yield important insight into the electrophysiology of the myocardium, including parameters that quantify the phase of the Action Potential ("AP") that is exhibiting an alternating pattern and the degree of zonal disassociation across the heart (i.e.: out of phase alternans across the heart that may be the source trigger for re-entrant arrhythmias). These additional data may lead to an improved method for patient risk stratification and a lower indeterminate threshold. Various features of the invention are directed to methods for determining T-wave alternan signatures (i.e., morphology and polarity) derived from a physiologic signal representative of a subject's heart activity; assessing changes in the myocardium Action Potential ("AP") through analysis of the alternan signature derived from a physiologic signal representative of a subject's heart activity; and/or assessing spatial disassociation of alternan characteristics that are likely associated with the initiation of re-entrant arrhythmias.

As will be discussed in more detail below, some or all of these features can be used to assess the cardiac condition of a subject. In all embodiments, an estimated T-wave alternan signature for a given heart rate is needed. This estimated T-wave alternan signature includes derived waveform morphology (signal) while preserving the polarity of the waveform, which provides data heretofore unavailable by the prior art methods of cardiac assessment through T-wave analysis. Robust embodiments include multiple T-wave alternan estimates for multiple heart rates across at least one signal source, such as at least one conventional ECG Stress test lead.

In certain embodiments, a physiologic signal representative of a subject's heart activity is acquired and the T-wave component of selected heartbeats is identified. The T-wave components of adjacent heartbeats are differenced to obtain a gross estimate of resultant alternan signatures. The gross estimate is constructed to include and preserve amplitude polarity information. At least one and preferably several signal processing functions are performed to derive at least one desired alternan signature estimate for the selected heart beats, which is statistically correlated to and representative of the alternan signature of the selected heart beats.

The derived alternan estimate is preferably one of many such estimates representative of various cardiac conditions induced by stress testing the subject. A feature of an embodiment of the invention relates to the reporting of the derived data. For example, an embodiment of a reporting feature includes the simultaneous visual display of a plurality of derived alternan signature estimates in matrix form. In such an embodiment, the plurality of derived alternan estimates are associated with a corresponding plurality of heart rates by displaying temporally adjacent estimates adjacent to one another. In this manner, an analyst is readily able to discern changes in the alternan waveform morphology over the range of heart rates being reported. Moreover, the reporting feature can further include simultaneously displaying visual representations, either numerically or graphically, of the relative alternan waveform amplitudes derived from each physiologic signal. For example, a plurality of alternan waveform estimates derived from a plurality of ECG leads are presented in such a format.

Another feature of several embodiments of the invention is to normalize the acquired data to provide a better correlation between the alternan estimate and the actual heart condition. Motion artifacts, muscle artifacts, system noise, respiratory artifacts or other noise present in at least one physiologic signal representative of a subject's heart activity can obscure the alternan estimate. To mitigate such noise, the acquired data is normalized so that the alternan estimate more closely correlates to the actual condition of the subject's heart. In one embodiment of the normalization procedure, systemic amplitude fluctuations and baseline wander in the waveform are characterized. The associated effects on the signal are then minimized by correcting for amplitude gain and DC bias to achieve a more accurate alternan estimate for a plurality of repeating waveforms.

Several embodiments of the invention also increase the real-time reporting ability of certain results and reduce random or stationary noise by smoothing and sub-sampling the gross alternan estimates. Such noise reduction can be achieved by calculating median or average values and curve fitting using first or second order polynomials. In a preferred embodiment, time domain segments (time bins) of a given alternan estimate are established, which preferably reduce the number of data points to about 15 to 25. Suitable noise reduction algorithms, such as those described above, are applied to each time bin, thereby yielding a smoothed estimate of the alternan signature of interest. This method is then applied to a suite of temporally adjacent alternan estimates until a desired number of alternan estimates have been derived.

The usefulness of the smoothed alternan estimates can be enhanced by obtaining a reference curve from these estimates, such as by averaging the curves or preferably finding the median curve. From this reference curve, a weighting factor can be established and used to determined a weighted average alternan estimate of the suite of smoothed alternan estimates derived above. In a specific embodiment, the root mean square (RMS) of the difference between the reference curve and each of the smoothed T-wave alternan estimates from the suite of heartbeats is determined. Smoothed alternan estimates that are similar to the reference curve, i.e., those wherein the RMS value is small, are weighted more heavily than those that are dissimilar to the reference curve, i.e., those wherein the RMS value is large. The derived weighting factor is then applied to each alternan estimate and the weighted smoothed estimates averaged to yield a robust alternan estimate for the suite of heartbeats under consideration, or portions thereof.

Yet another feature of several embodiments of the invention manages or otherwise compensates for disruptive events, such as premature beats, pauses or other disruptions to a steady cardiac rhythm, that may reverse the polarity of the alternan signature. Adjustment for the presence of disruptive events is generally desirable for many polarity sensitive embodiments of the invention. By monitoring the polarity of each alternan signal within a suite of heartbeats, adjustments to the polarity of alternan estimates following a disruptive event can be applied.

Still another feature of a specific embodiment provides a basis for associating certain types of alternan signatures with physiological changes in the action potential (AP) of a subject's heart. It has been found that a relationship exists between epicardial AP alternations and T-wave alternans. For example, the three major forms of epicardial AP alternations, i.e., depolarization, refractory, and repolarization phases, are associated with three distinct T-wave alternan signatures. An aspect of this feature is to ascertain data from the T-wave alternan estimates that represent specific characteristics of AP alternations. In one embodiment, at least three model curves are established that represent the alternation in ECG signal associated with alternation in each phase of the AP. Through a simultaneous curve fitting method, the estimated alternan signal is decomposed into components representing the contribution from each of the three distinct AP processes. Thus, by analyzing the waveform of a T-wave alternan estimate, one is provided with information regarding the affected phase of the epicardial AP. Risk estimates of cardiac instability may be developed from these distinct estimates of AP alternation.

Preserving the full waveform of the alternan signal, including recording consistent amplitude polarity, supports an assessment of cardiac alternan disassociation wherein distinct regions of the heart display different alternan characteristics. These out-of-phase alternan patterns establish voltages across regions of the heart and may trigger arrhythmias. A risk assessment method can then be developed that quantifies the severity of the alternan disassociation based upon the simultaneous voltage differences of the alternan signatures and the spatial separation of the regions sampled by the distinct physiologic signals.

An embodiment of one method for determining T-wave alternan signatures in accordance with the invention comprises: (1) acquiring electrophysiological data (a beat series) from a subject's heart of sufficient duration wherein such data includes electrical signals corresponding to T-wave data found in an electrocardiogram ("ECG"); (2) identifying T-wave segments within the beat series data for use in the analysis that account for ectopic beats and other significant changes that may disrupt the alternan pattern; (3) correcting the data for baseline wander and motion artifacts associated with respiration and other noise; (4) differencing adjacent beats within the beat series while retaining polarity and morphology information to compute initial estimates of the alternan signature for the series; and (5) smoothing and stacking the individual estimates to lower noise and provide a robust estimate of the alternan signature for the beat series. This method can further comprise (6) decomposing the alternan signature into components related to changes in the depolarization, refractory and repolarization components of the myocardium AP; and/or (7) reporting the alternan signatures. In addition, optional procedures can be employed to assess the severity of spatial disassociation of the alternan signature in other embodiments of methods in accordance with the invention.

DETAILED DESCRIPTION

The following discussion is presented to enable a person skilled in the art to practice the invention. Various modifications to the disclosed embodiments will be apparent to those skilled in the art, and the generic principles herein may be applied to other embodiments and applications without departing from the spirit and scope of the present invention as defined by the appended claims. Thus, the present invention is not intended to be limited to the embodiments presented, but is to be accorded the widest scope consistent with the principles and features disclosed herein.

Figure 1A:
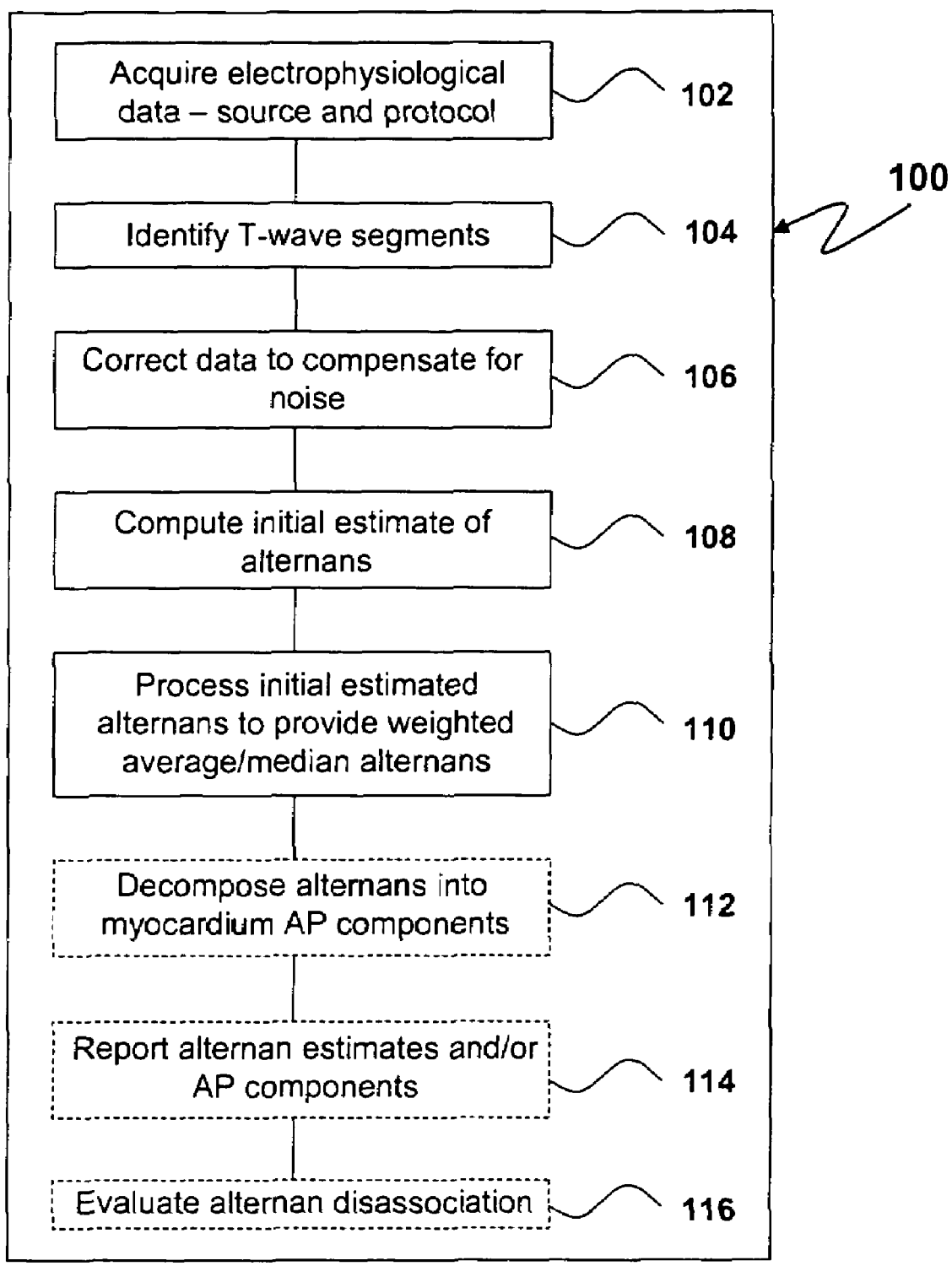
FIG. 1A is a flow chart illustrating a method for determining and representing a T-wave alternan estimate in accordance with an embodiment of the invention.
Figure 1B:
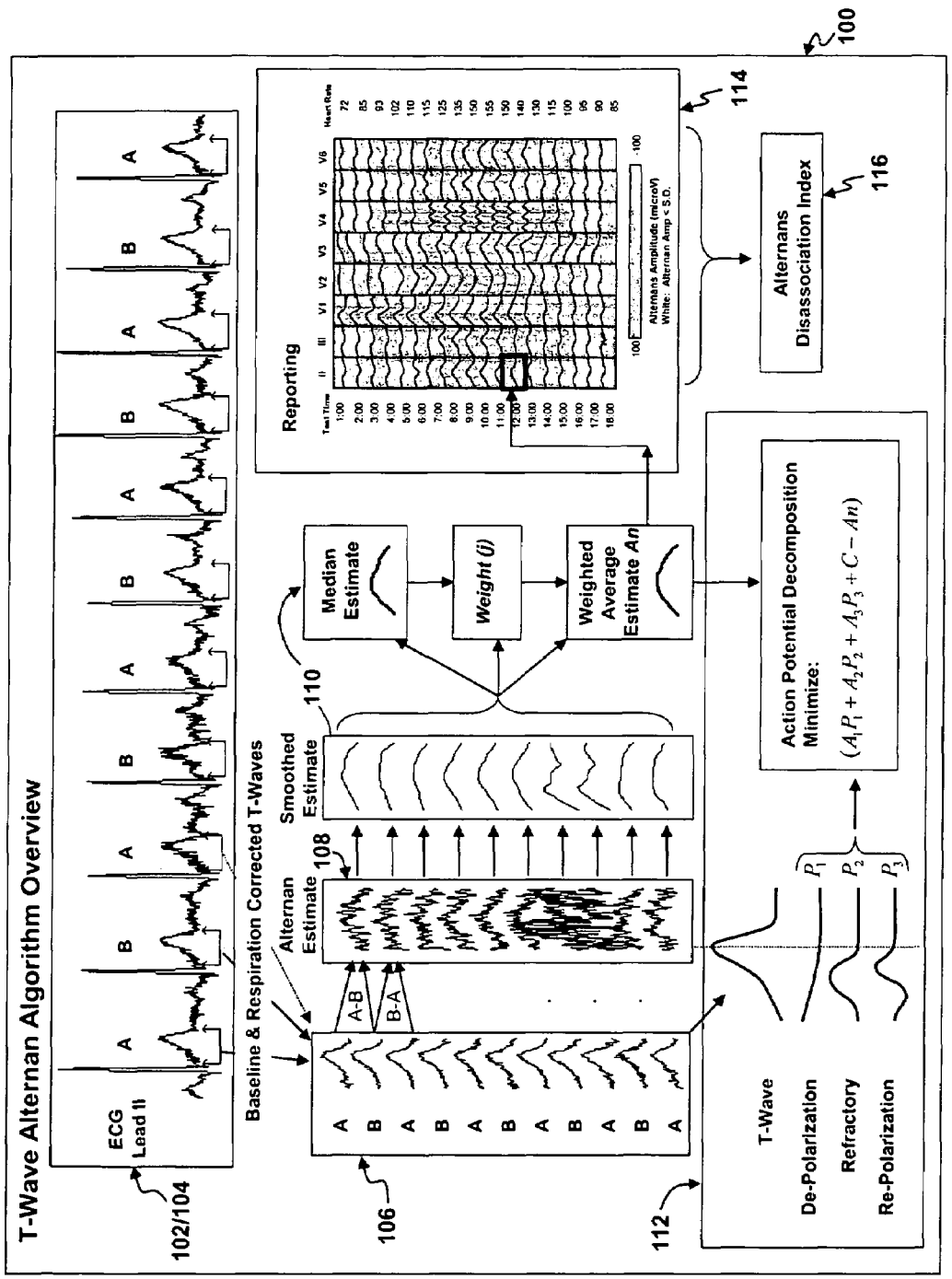
FIG. 1B is a diagram schematically illustrating stages of the method for determining and representing an alternan estimate in accordance with the embodiment of the invention shown in FIG. 1A.

FIG. 1A is a flow chart of a method 100 for determining and representing a T-wave alternan estimate in accordance with an embodiment of the invention, and FIG. 1B is a diagram schematically illustrating the stages of the method 100 shown in FIG. 1A. Referring to FIGS. 1A and 1B together, the method 100 includes a first stage 102 comprising acquiring electrophysiological data (e.g., a heartbeat series) of sufficient duration to include electrical signals corresponding to T-wave data. The method 100 also includes a second stage 104 comprising identifying the T-wave segments within the series of heartbeats. The second stage 104, for example, can further include assessing the identified T-wave segments to compensate for ectopic beats and other significant changes that may disrupt the alternan pattern. Referring to FIG. 1B, the first stage 102 and second stage 104 are graphically illustrated using an electrocardiogram (ECG) readout in which the T-wave segment is identified for sequential heartbeats A and B by bracketed arrows.

The method 100 continues with a third stage 106 that includes correcting the acquired data for baseline wander and motion artifacts caused by respiration, movement and other sources of noise. The third stage 106 in FIG. 1B graphically illustrates subsequent T-wave segments that have been corrected for baseline wander and artifacts caused by such noise. After the third stage 106, the method includes a fourth stage 108 in which initial estimates of the alternans between subsequent beats are calculated, and a fifth stage 110 in which the estimated initial alternans are smoothed and stacked to further lower the noise and provide a more robust estimate of the alternan signature for a series of heartbeats. The fourth stage 108 can include computing the initial estimate of the alternans by calculating the differences between adjacent T-wave segments within the beat series at common respective time intervals in a manner that retains the polarity and morphology information. The fifth stage 110 can further include (a) providing a median estimate, (b) weighting the median estimate, and then (c) determining a weighted average estimate of An alternans.

The method 100 can optionally include a sixth stage 112 comprising decomposing the alternan signature into components related to changes in the (a) depolarization, (b) refractory, and (c) repolarization components of the myocardium action potentials (AP). The sixth stage 112 can accordingly determine different action potential decompositions relative to the weighted alternan average An to provide specific information to evaluate a patient as described in more detail below. Several embodiments of the method 100 also include a seventh stage 114 in which the alternan signatures for various electrodes are reported to an operator. As shown in FIG. 1B, the seventh stage 114 can report the alternan signatures in a graphical display illustrating the weighted average alternan estimate An for a number of electrodes during a stress test. An eight stage 116 further processes the data from stage 110, for all leads and all time intervals, to derive a measure of spatial disassociation of alternan voltages for use in assessing patient risk from arrhythmias.

The embodiment of the method 100 shown in FIGS. 1A–1B is broken down into discrete steps illustrating one embodiment of a series of steps that achieve certain benefits of the invention. Other embodiments of methods in accordance with the invention may not include all of the stages 102–116 and still achieve several benefits of the embodiment shown in FIGS. 1A–B. For example, if suitable digital ECG data is already available, it is not necessary to create the data and certain steps need not be performed in order to achieve the benefits of the invention. The following discussion accordingly describes several of the stages 102–116 of the method 100 in greater detail with the understanding that the individual stages can be eliminated or use other processes in other embodiments of the invention.

A. Data Source and Protocol

The first stage 102 of the embodiment in this method 100 shown in FIG. 1A involves acquiring electrophysiological data from a data source using a suitable protocol. Clinically useful estimates of low amplitude alternan signals preferably require a contiguous heartbeat series of 64–128 beats with an approximately constant heart rate. The number of contiguous beats may be in the range of 16–32 in the presence of low noise, and in exceptional conditions could be as low as 2 beats. Because of the very low voltages being analyzed, robust methods for reducing noise at all stages of data acquisition and processing is highly desirable. While some sources of noise cannot be reduced (see below), good ECG electrode preparation such as with Quinton Cardiology Inc.'s QUICKPREP® will significantly reduce the level of noise relating to the electrode-subject interface. Details of this product and related methods of use can be found in commonly owned U.S. Pat. No. 5,458,141, which is incorporated by reference. In addition or alternatively, monitoring of electrode impedance and noise during application will contribute to overall noise reduction.

Noise directly affects the length of the beat series used to compute alternan estimates. Stationary noise not linked with or created by the beat should decline approximately as the square root of the number of beats included in the series— e.g.: 16 beats should lower the noise by about a factor of 4, and 64 beats should lower noise by about a factor of 8. A dynamic assessment of noise conditions during data acquisition and processing can be used to establish the number of beats necessary to provide reliable data. Because ectopic beats and other cardiac events (e.g., a pause or a rapid change in R—R interval) can disrupt the alternan pattern, minimizing the number of consecutive beats required to obtain reliable results affords more opportunity for diagnosis of subjects with higher incidences of ectopic heart beats.

Noise can be generated from a multiplicity of sources and therefore the identification and suppression, conditioning and/or filtering of such noise is desirable. Common sources of subject-related noise include motion artifacts (movement of the heart within the pericardial cavity or chest movement induced by body impacts encountered from walking or running during a treadmill stress test); surrounding muscle contraction artifacts from body and arm motion; breathing or respiration artifacts (both from the change in chest impedance and the repositioning of the heart within the chest as the lungs inflate); and, electrode-skin contact noise.

Some subject-related noise suppression and/or conditioning is relatively easy to achieve and include actions such as having the subject minimize and/or keep constant the rate of body impacts during testing; maintaining a constant rate of physical exertion (e.g., a constant pace of walking on a treadmill); attempting to maintain a relatively constant respiration rate; etc. The conditioning generally attempts to eliminate or stabilize the frequency, duration, and/or amplitude of the noise, which facilitates noise identification and removal. Thus, increasing the rate of physical exertion during stress testing by having the subject maintain a constant pace while increasing the elevation of a treadmill is one means for conditioning the noise for later filtering (and thus suppressing the effect of that noise). A derivative of this approach is to monitor the heart rate and dynamically adjust the grade of the treadmill to maintain the target rate, thereby eliminating the variables associated with a non-stable heart rate during the data acquisition phase.

In addition to external sources of noise, there is clinical/laboratory data that suggests ectopic beats and other cardiac events may re-set the alternan signal (i.e., the alternan signal may shift a beat, switching from an even-odd pattern to an odd-even pattern, thus disrupting the analysis). Therefore, contiguous beat sequences should be selected for analysis that exclude ectopic beats or other disruptions. For subjects with a high ectopic rate it is necessary to extend the analysis by combining multiple shorter beat sequences and using correlation methods to determine the possible polarity change for each sequence associated with a changing beat pattern, as discussed below.

A preferred stress profile to induce an alternan response is to place a subject on a controllable, variable speed treadmill with a variable incline feature such as the Q-Stress® cardiac stress testing system manufactured by Quinton Cardiology, Inc. The data acquisition protocol is preferably similar to a standard Burke protocol, beginning with the subject at rest and recording a suite of heartbeats for about 2–3 minutes. Next, the subject's heart rate is increased by increasing the treadmill grade and then held constant for about 2–3 minutes, during which time another suite of heartbeats is recorded. This progression continues until the desired maximum heart rate is achieved or the subject is exhausted. Maintaining a constant treadmill speed, and thus a constant pace, while increasing the grade stabilizes noise associated with body motion artifacts and improves the estimate of alternan signature associated with increasing heart rate. Alternatively, but with somewhat higher motion noise associated with increasing heart rate, other protocols such as the Bruce protocol could be used to exercise the subject, where both the speed and grade are adjusted periodically until the subject either reaches the desired maximum heart rate or is exhausted.

B. Cross-Correlation and T-Wave Selection

After successfully recording appropriate ECG samples or retrieving such samples from stored data at each desired heart rate, the method 100 continues with the second stage 104 by ascertaining the alternan component between temporally adjacent T-waves. One aspect of this stage is consistently selecting from beat to beat the onset time of the T-wave segment. The amplitude of the T-wave is very large compared to the alternan heartbeats signal. In general, the T-wave may have an amplitude of 300–1000 microvolts; the alternan signal computed from the difference of adjacent T-waves may have an amplitude of only a few microvolts. A mis-alignment of the T-wave between two adjacent beats of 2.0 milliseconds (the standard sampling rate for stress testing) can produce a false amplitude anomaly of 5–10 microvolts. Therefore, it is important to use a high sampling rate, e.g., 0.5–1.0 millisecond, and to accurately align the T-waves in order to measure the signal and not be overwhelmed by processing noise associated with mis-alignment of the T-waves from beat to beat.

Figure 2A:
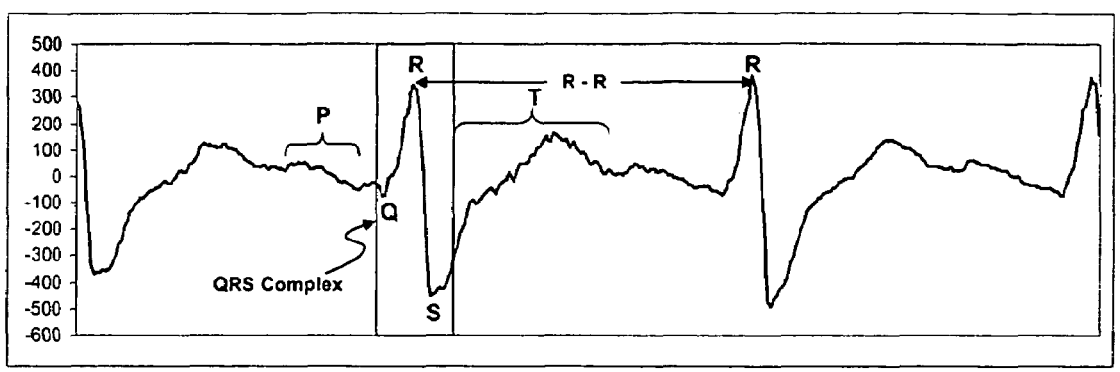
FIG. 2A is a graph illustrating an ECG and the reference points corresponding to activation and recovery of the Atria (P); the ventricle activation phases Q, R and S, forming the QRS complex; the recovery or re-polarization phase T of the ventricles; and the R—R time interval between consecutive beats as measured between the peaks of the R phase.

FIG. 2A illustrates an example ECG with the key phases identified. The normal heart beat starts in the upper chambers of the heart (atria) and the initial ECG phase that records this activation is termed the P-wave; the bracket indicates the duration of the P-wave. Following the activation of the atria the blood moves into the lower chambers of the heart (ventricles) and activation of the ventricle muscle both pumps the blood to the body and generates the ECG phases Q, R and S, often referred to as the QRS complex. Finally, the ventricle muscles recover (repolarize) in anticipation of the next beat, creating the T-wave signal on the ECG. The time interval between adjacent beats is generally measured between the peaks of the R-wave and is referred to as the R—R interval. The letter designations are commonly used to also specify specific segments of the ECG.

For instance, the PQ interval would be the segment that begins with the onset of the P-wave and concludes with the Q-wave.

Figure 2B:
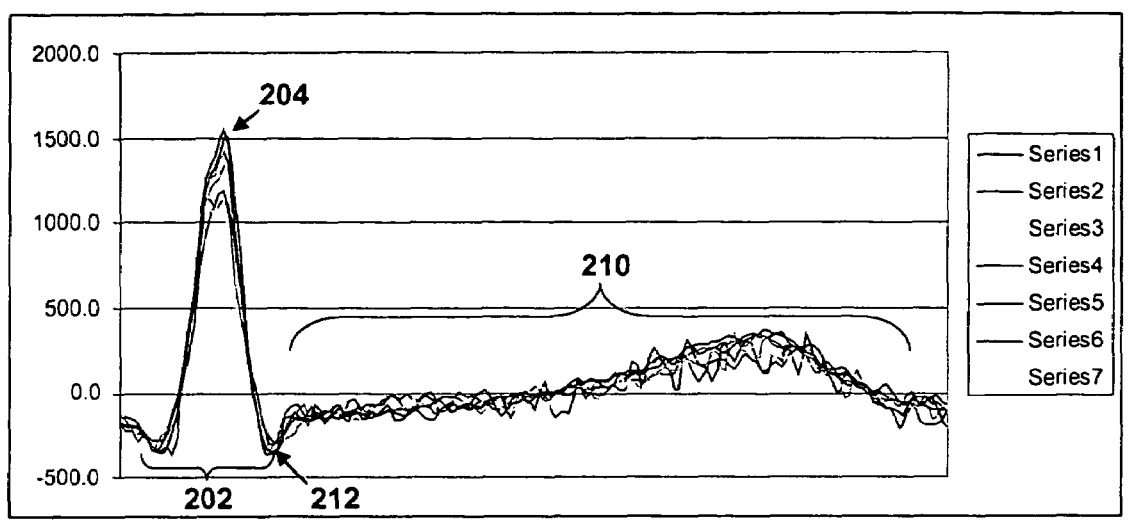
FIG. 2B is a graph showing the alignment of QRS complexes from a cross-correlation.

FIG. 2B illustrates an example of aligned waveforms from a series of heartbeats. The waveforms have a QRS complex 202 with an R-wave peak 204. For a sequence of beats to be analyzed for an alternan signal, the following steps are preferably used to select the T-wave segment within each beat in a beat series.

1. Using the R-wave peak 204 within the QRS complex 202 to approximately time align each beat, compute a median beat estimate for the selected sequence of beats for at least one, and preferably all, ECG leads.
2. Window the QRS segment from the median beat estimate computed in step 1 and cross-correlate this windowed QRS pulse with the ECG data, finding the peaks in the cross-correlation. Preferably, the cross correlation metric should be based upon the peak of the sum of the cross correlations across leads I, II, and V1–V6—i.e.: the selected QRS correlation time point should be the same across all leads.
3. Use the refined QRS onset time from step 2 to re-stack the data, using either an average or median stack, thus developing an improved estimate of the QRS complex.
4. Using the improved QRS estimate, repeat steps 2 and 3 above, resulting in a final estimate of QRS onset time for all beats in the sequence and all traces and a best estimate of the QRS complex morphology. Save the QRS complex for further use in computations discussed below.
5. The T-wave 210 for each lead is preferably selected based on the following parameters:
   a. The onset time should be a few samples beyond the maximum negative excursion of the S-wave 212 (and the same across all leads).
   b. The duration of the T-wave, and hence the end time, is more complex. Preferably, the analysis uses the entire T-wave, but it is helpful to maintain a constant T-wave window length over the entire test analysis. As heart rate increases, the P-wave for the next beat may start to ride on the end of the T-wave from the previous beat, adding noise to the analysis. The target heart rate and the associated estimate of the duration of the R—R interval ($D_{R-R}$) at peak exercise, along with the duration of the interval from the onset of the P wave to the end of the S phase ($D_{P-S}$), should be used to compute a maximum window length for the T-wave (Maximum Length=$D_{R-R}$-$D_{P-S}$). The T-wave window length should be computed from the initial (resting) data and held constant for the entire test. Preferably, the end of the windowed T-wave should be well beyond the peak of the T-wave—as discussed below, most of the alternan signal will be in the segment between the end of the S-wave and the peak of the T-wave.

The cross-correlation times of the QRS complex also form the basis for tracking R—R intervals and associated dispersion, and for identifying anomalous pauses or jumps in heart rate that may re-set the alternan signal. The cross-correlation times are useful in this analysis and are generally retained for subsequent use.

C. T-wave Normalization for Baseline Wander

Figure 3:
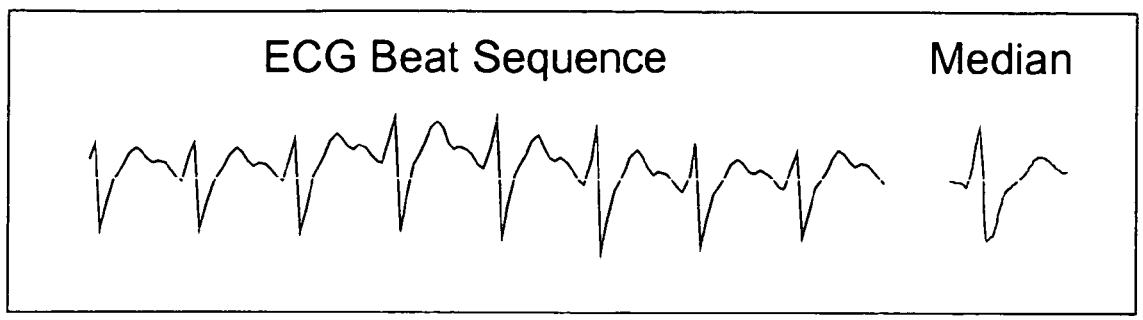
FIG. 3 is a graph illustrating a sample ECG Beat Sequence and a computed Median beat in accordance with an embodiment of the invention.
Figure 4:
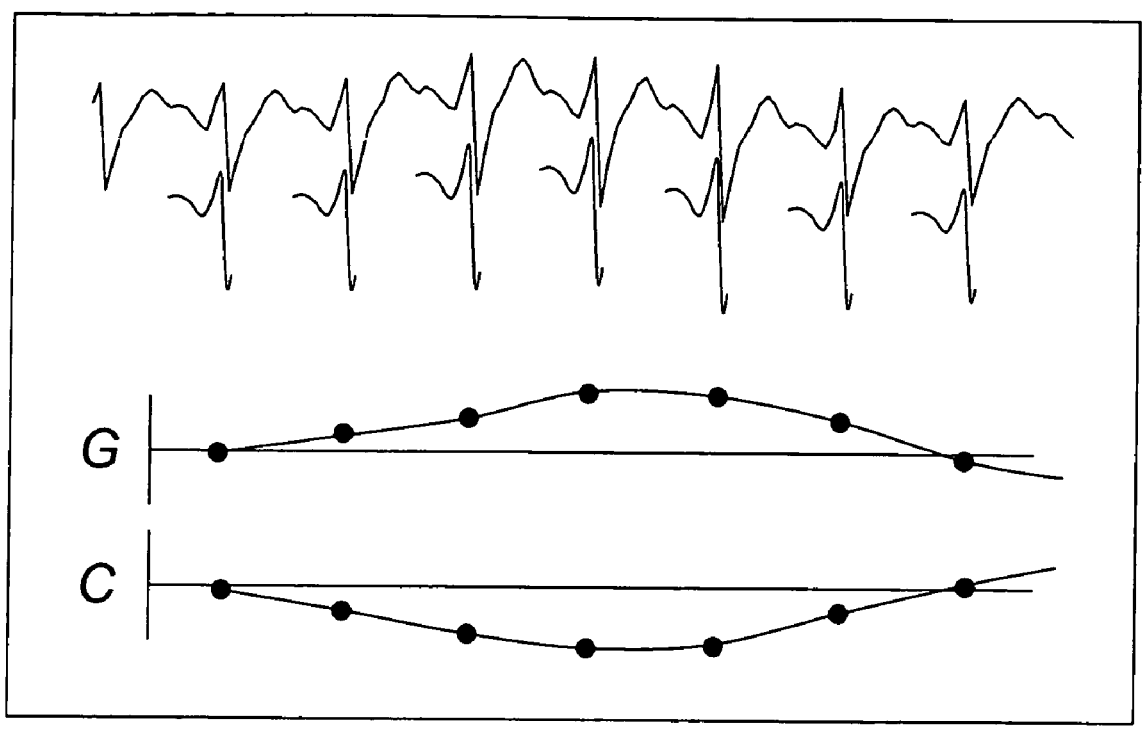
FIG. 4 shows the alignment of the P-S signature of the average beat (Ave(i)) with the beat sequence and the resulting amplitude and DC offsets (G and C respectively) that mitigates the RMS error between the average and the beat sequence in accordance with an embodiment of the invention.

The third stage 106 of the method 100 processes the data to mitigate the affects of noise. The ECG data is influenced by many sources of noise, including high frequency muscle artifact and system noise as well as long period noise associated with respiration and body movements. Referring to FIG. 3, the raw ECG data typically includes both a baseline wander and amplitude variations associated with respiration. In this figure the amplitude variations can be seen by examining the difference between the peak of the R-wave and the trough of the S-wave; this difference is smallest for the beats on the left and right side of the figure and maximum for the beats in the central portion of the ECG. This figure also illustrates baseline wander as detected by observing how the onset of the QRS complex rises for the central beats and falls for the beats on the left and right sides of the ECG. Even though the ECG data includes such baseline wander and amplitude variations, a robust estimate of the average or median beat, Ave(i), can be computed, as discussed in the previous section, and is shown adjacent to the ECG trace The average or median beat Ave(i) estimate can be compared with the individual beats to derive an amplification gain factor and a DC shift factor. For example, the median or average beat, Ave(i), can be scaled by an amplification factor G(m) and DC shift factor C(m) to minimize the least square difference with each beat in the sequence. To mitigate or prevent introducing systematic bias or noise into the T-wave portion of the signal, the minimization window should focus on just the P-S beat segment and solve for the optimal G and C for each beat, as illustrated in FIG. 4.

The system of equations to be solved for each beat are:

$$G \times Ave(i) + C = ECG(i)$$

In matrix notation the least squares solution to this system of equations is:

$$\begin{pmatrix} G \\ C \end{pmatrix} = \begin{pmatrix} \sum_n Ave^2(i) & \sum_n Ave(i) \\ \sum_n Ave(i) & n \end{pmatrix}^{-1} \begin{pmatrix} \sum_n Ave(i)ECG(i) \\ \sum_n ECG(i) \end{pmatrix}$$

where n is the number of data points in the P-S interval. Solving for the inverse yields:

$$G = \frac{n \sum_n Ave(i)ECG(i) - \sum_n Ave(i) \sum_n ECG(i)}{n \sum_n Ave^2(i) - \left(\sum_n Ave(i)\right)^2}$$

$$C = \frac{\sum_n Ave^2(i) \sum_n ECG(i) - \sum_n Ave(i) \sum_n Ave(i)ECG(i)}{n \sum_n Ave^2(i) - \left(\sum_n Ave(i)\right)^2}$$

Once G and C are derived for each beat, a cubic polynomial function ($F_C$ and $F_G$) can be computed that smoothly connect four values of G or C associated with four consecutive beats. The computed middle segment of the resulting function, between the second and third values for G or C, is used to correct for gain and DC bias for the T-wave in this segment, following:

$$ECG_{corrected}(i) = \frac{ECG(i) - F_C(i)}{F_G(i)}$$

Figure 5:
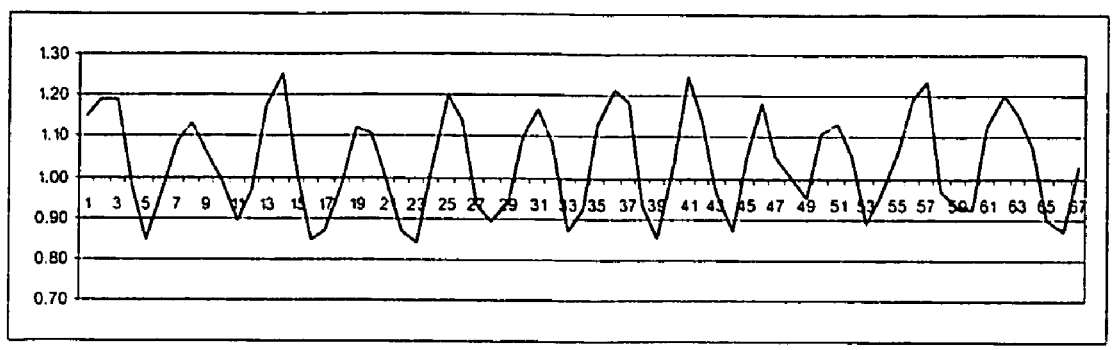
FIG. 5 is a graph illustrating the computed gain for a sequence of beats that mitigates the amplitude and baseline wander associated with the respiration signal contained in the ECG in accordance with an embodiment of the invention.

As noted by many previous investigators (see, e.g., Moody et al., "Clinical Validation of the ECG-Derived Respiration (EDR) Technique," Computers in Cardiology, p 507–510, 1986, which is incorporated by reference), the ECG signal is modulated by respiration. The amplitude variations are caused by mechanical movement of the electrodes relative to the heart, rotation of the heart within the chest, and changes in chest impedance as the patient breathes. The herein computed gain for each beat can also be used to derive the respiration rate. The curve shown in FIG. 5 is the computed gain for an example ECG, the numbers along the X-Axis are the beat sequence numbers.

The instantaneous respiration rate can be computed by measuring the time between peaks (e.g.: 7 seconds/breath) or by averaging the rate over longer time periods. Alternatively, the peak in the Fourier transform of this series (i.e.: the series constructed from the consecutive gain correction values for each beat) provides an estimate of the respiration rate. The energy at the Nyquist frequency also provides an estimate of the respiration noise that has an alternans rate. These derived estimates of respiration rate are preferably included in the noise analysis and estimation of alternans reliability.

D. T-wave Alternan Estimate

After extracting the T-waves from a contiguous suite of non-ectopic beats in the second stage 102 and processing the data to compensate for baseline wander and systematic amplitude variations in the third stage 104, the waveform difference between the adjacent beats is next computed in the fourth stage 108. This difference in waveforms for adjacent heart beats provides an initial estimate of the T-wave alternans. More specifically, T-wave alternans are characterized by an amplitude of the T-wave that is alternating every other beat. For example, in the beat sequence 1, 2, 3, 4, 5, . . . the even beats would have an amplitude augmentation relative to the odd beats. Hence, estimates of the alternans are computed through difference of the even beats minus the odd beats. For a sequence of m beats, 1, 2, 3, 4, 5 . . . the alternans estimates are:

(2-1), (2-3), (4-3), (4-5) and so on.

Re-ordering, this is:

(2-1), −(3-2), (4-3), −(5-4) and so on.

So, the jth estimate of the alternans, at time position i in the T-wave, can be computed from the normalized T-waves from each beat by:

$$\text{Alternan}(i,j) = (-1)^j (T(i,j) - T(i,j-1))$$

E. Smoothing and Sub-Sampling the Alternan Estimates

The method 100 continues with the fifth stage 110 by smoothing, sub-sampling, and further refining the alternan estimates. The above computed estimates of the alternans will typically contain about 600–700 data points (at 2000 samples per second). The alternan signal has a somewhat longer period, relative to the 1000 Hz Nyquest frequency of the raw ECG data, and smoothing of each individual alternan estimate is an effective way to further reduce random or non-stationary noise. Computationally, it is preferable to reduce the number of data points that are used in the subsequent computations to a number in the range of 15–25 (an odd number being desired).

Figure 6:
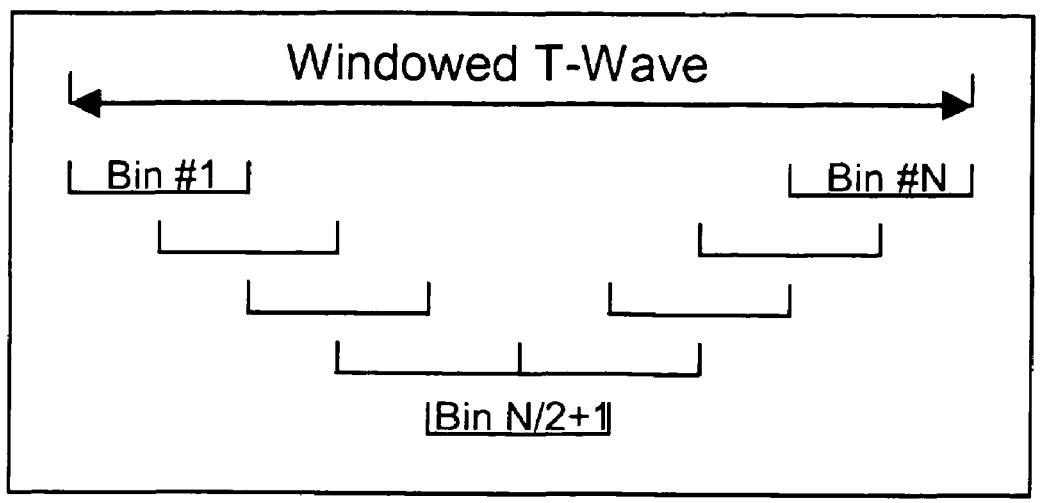
FIG. 6 is a schematic illustration showing an example of overlapping windows used to bin and smooth the alternan estimate data in accordance with an embodiment of the invention.

Referring to FIG. 6, the alternan estimate computed over the duration of the windowed T-wave can be divided into bins of data. A simple median or average over the specified time bins usually provides sufficient smoothing. However, a first or second order polynomial may also be fit through the data and the mid-point of the fitted curve used as the average value for the bin. The bins should be overlapping and follow the general structure illustrated in FIG. 6.

This procedure reduces the estimate of the alternans to around 21 points that spread uniformly over the duration of the alternan signal. This also improves the signal to noise ratio by approximately a factor of 5. Clearly, the number of bins and the bin lengths can be adjusted as appropriate for the length of the alternan estimate. In general, an odd number of bins in the range of 15–25 provides acceptable smoothing while retaining the complex morphology of the alternan signal. The smoothed alternan estimate is designated as Alt_Smoothed(i,j), where i is the time position ranging from 1 to about 21 for the jth alternan estimate.

Figure 7:
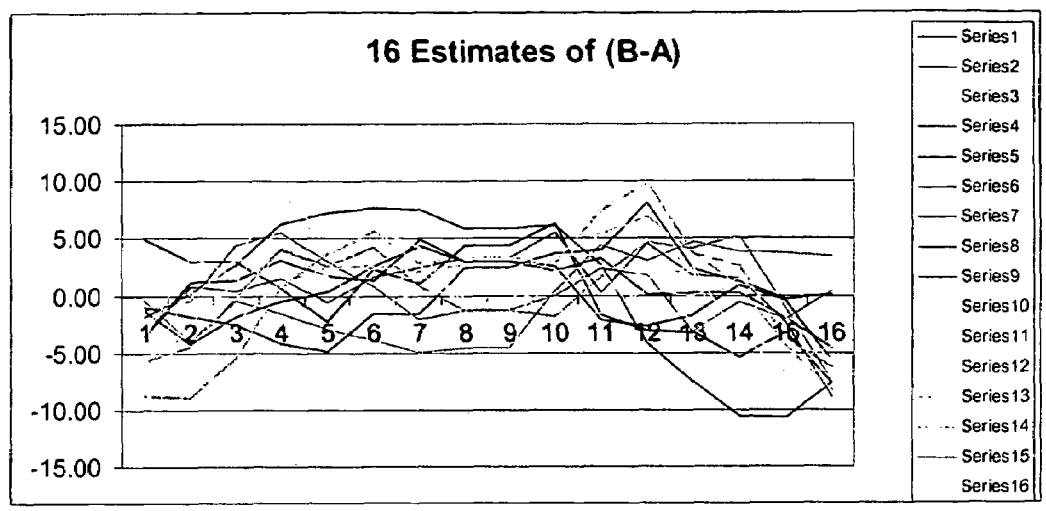
FIG. 7 is a graph showing sixteen individual smoothed estimates of alternan signature computed from 17 successive beats in accordance with an embodiment of the invention.

The plot in FIG. 7 illustrates 16 individual smoothed alternan estimates, Alt_Smoothed(i,j=1,16), smoothed from an initial 160 points. Although each smoothed alternan estimate still displays noise, the general fabric of the alternan signal is beginning to emerge in the 16 independent estimates.

F. Median Estimate of the Alternans

The fifth stage 110 can further include determining a median estimate of the alternans over a period of several heart beats. The above discussed processing can be computed for a contiguous suite of beats, resulting in a suite of smoothed estimates of the alternan signal. In general, the signal to noise level from any single estimate will still be quite low and ensemble averaging of many estimates, perhaps as high as 128 depending upon noise conditions, may be necessary. It is also common to have occasional noise bursts that are localized in time, e.g., a muscle artifact spike, causing estimates computed from the affected beat to be exceptionally noisy. The exceptionally noisy estimates resulting from noise spikes can be identified and suppressed, and/or prevented from significantly lowering the signal to noise enhancement that should be obtained from normal signal averaging. This can be accomplished by a two step process. First, an approximate estimate of the alternan signal is developed, and then a weighted average computation is performed based upon the root mean square (RMS) difference between the estimate for the suite and an individual estimate. The estimate for the suite preferably uses a median estimate, Median(i), as it is robust in the presence of occasional noise bursts.

G. Weighting Estimates

After determining the median estimate of the alternans, the fifth stage 110 can continue by weighting the individual smoothed alternan estimates. The median estimate established previously may not be useful by itself; however, it finds utility with respect to establishing a weighting factor for each of the smoothed alternan estimates. This weighting factor is preferably used in averaging the individual smoothed alternan estimates. To establish the weighting factor, the RMS of the difference between the median estimate, Median(i), and each of the individual smoothed alternan estimates, Alt_Smoothed(i,j), are computed. When the RMS is large (i.e. the smoothed alternan estimate is substantially different from the median estimate), the weighting factor for the alternan estimate is low, and vice versa. The weighting factor for the jth alternan estimate is defined as:

$$\text{Weight}(j) = \left(\left(\frac{1}{n}\right)\sum_{i=1}^{n}(\text{Median}(i) - \text{Alt\_Smoothed}(i, j))^2\right)^{-\frac{1}{2}}$$

The weighting factors may be adjusted such that 5–10% of the alternan estimates that best fit the median estimate are uniformly weighted; strict adherence to the weighting equation could lead to an exceptional weight for the chance case where an estimate nearly exactly equals the median.

H. Weighted Average Estimate of the Alternan Signal

The fifth stage 110 can further include determining a weighted average estimated alternan An. Using the smoothed alternan estimates and the associated weighting factors, the weighted best estimate for the smoothed alternan signal is:

$$An(i) = \frac{\sum_{j=1}^{m} \text{Alt\_Smoothed}(i, j) \times \text{Weight}(j)}{\sum_{j=1}^{m} \text{Weight}(j)}$$

The Standard Deviation should be computed from:

$$S.D. = \left[\frac{1}{\sum_{j=1}^{m}\text{Weight}(j)}\sum_{j=1}^{m}\text{Weight}(j) \times \left(\frac{1}{n}\sum_{i=1}^{n}(An(i) - \text{Alt\_Smoothed}(i, j))^2\right)\right]^{\frac{1}{2}}$$

for m estimates of the alternan signal at n values for each individual estimate. Weight(j) is defined above. The industry standard gross estimate of the alternan amplitude may be computed from An(i) by:

$$Amp = \frac{1}{2 \times n}\sum_{i=1}^{n}|An(i)|$$

Figure 8A:
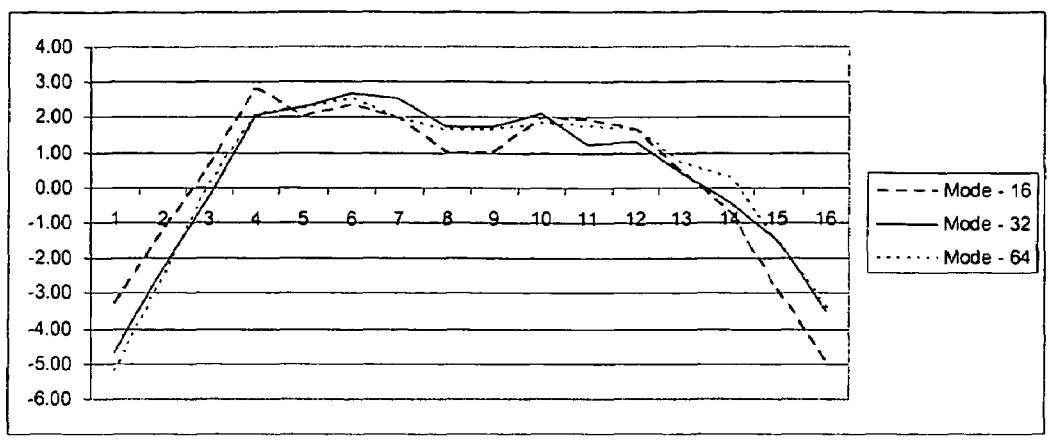
FIG. 8A is a diagram showing the estimates of smoothed alternan signatures computed from 16, 32 and 64 alternan estimates from successive beats in accordance with an embodiment of the invention.

The weighted stack can be computed over any number of estimates of the alternan signal. FIG. 8A shows computations from 16, 32 and 64 estimates of the alternan signal. A representative example of dispersion of the individual estimates is shown in the previous FIG. 7 for the 16 estimated averages (labeled "Mode-16").

I. Ectopic Beat Management

Figure 8B:
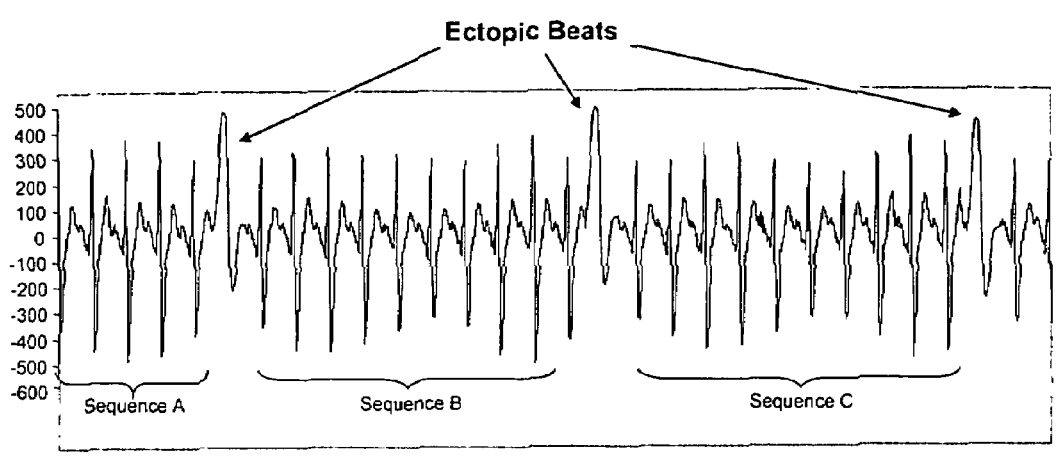
FIG. 8B is a graph illustrating an ECG signal interrupted by ectopic beats, dividing the entire sequence into multiple segments of contiguous beats.
Figure 8C:
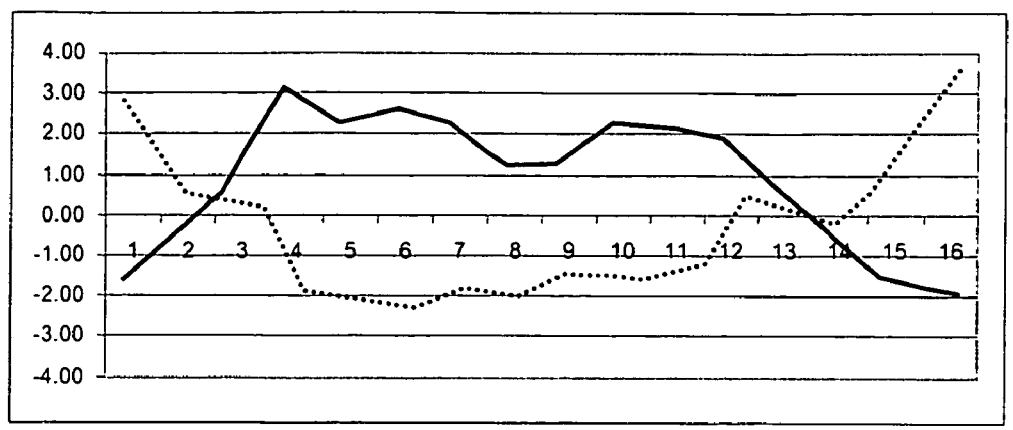
FIG. 8C is a diagram showing the polarity reversal of the smoothed alternan estimate that may occur when an ectopic beat or other disruption to the heart rhythm occurs.

Ectopic beats and other disruptions to a steady rhythm may cause a reset of the alternan signal, potentially changing from an odd-even-odd pattern to an even-odd-even pattern. FIG. 8B illustrates a beat sequence interrupted by three ectopic beats that segments the overall ECG into subsections of contiguous beats, marked as sequences A, B and C. The impact of a reset is to change the sign or polarity of the alternan signal as illustrated in FIG. 8C, i.e.: the morphology is "up-side-down" relative to the preceding pattern. As heart rate is the primary driver for triggering alternans, a reasonable assumption is that the underlying AP biophysics is unchanged by the event and the morphology, but not necessarily the polarity, is approximately stationary. This leads to a method to join together multiple shorter continuous beat sequences that have been interrupted. As suggested by FIG. 8C, the shape of the alternan signal can be used to determine if the polarity has changed after a disruptive event. If the cross correlation of the alternan estimates between the sequences before and after a disruptive event is greater than the cross correlation when one of the alternan estimates is reversed in polarity then no disruption has occurred. Algorithmically, if $$\sum_{k=1}^{8}\sum_{i=1}^{n}[An(i, k, \text{before}) \times An(i, k, \text{after})] >$$

$$\sum_{k=1}^{8}\sum_{i=1}^{n}[An(i, k, \text{before}) \times (-An(i, k, \text{after}))]$$

(where k is the lead number) is true then a polarity reversal has not occurred and the sequence of beats following the disruption can be used without correction. If this expression is false then a reversal has occurred and the polarity of the subsequent alternan estimates should be reversed for all leads after the disruptive event. This method can be used to improve signal to noise provided a rough estimate of the alternan morphology is emerging in the sequence in some of the leads. This method is employed by selecting contiguous beat sequences in stage 102, for instance segments A, B and C in FIG. 8B, that are not interrupted by ectopic beats or other disruptions, processing each sequence through stage 110, applying the above criteria to the weighted average alternan estimate computed for the first two sequences (A & B), correcting the second sequence if necessary for polarity reversal, and computing the ensemble weighted average for the two sequences. Using this combined estimate of the alternan signature, the polarity of the alternan estimate for the next sequence (e.g.: sequence C in FIG. 8B) can be assessed, corrected if necessary and combined with the estimate from the combined first two estimates. This method can be continued to each sequence in the selected ECG being processed in stage 102, thus increasing the overall signal to noise ratio of the alternan estimate. Short sequences may contain high noise that renders them of questionable value for inclusion in this process. The standard deviation estimate computed in stage 10, or other estimates of noise, may be used to decide when to exclude a sequence.

J. Best Fitting Model

In several embodiments, the method 100 also includes the sixth stage 112 of decomposing the alternans into components that can be correlated to specific conditions and specific areas. Before the present invention, the prior efforts to ascertain information from T-wave alternans looked only at changes in alternan amplitude, and this was done primarily over a narrow range of heart rates. However, it has been ascertained that T-wave analysis yields valuable information beyond simple amplitude related information. For some changes in the myocardium, the T-wave alternan signal will actually increase in some segments and decrease in others—the alternan signal is not just variability in peak amplitude, but includes changes in shape. It is therefore desirable to provide a means for associating the best estimate of the alternan signal (An) into an estimate of the nature of the AP alternation within the myocardium and an associated measure of uncertainty. To make this computation, several models for the T-wave alternan signals are provided and a procedure has been developed to systematically assess which model best fits the observations. This procedure associates features within the alternan signal with distinctly different phases of the myocardium Action Potential.

1. Action Potentials

Figure 9:
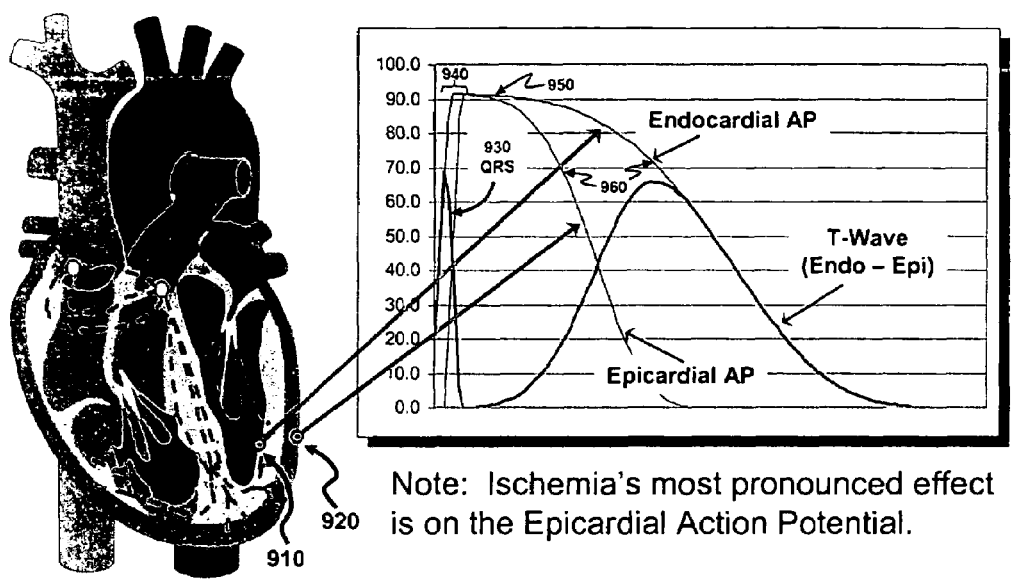
FIG. 9 is a graphic overlay of APs and T-wave formation wherein the T-wave represents the difference between the endocardial and epicardial APs in accordance with an embodiment of the invention.

The T-wave shape is strongly controlled by the shape of the APs of the cardiac tissue. The relationship between the AP and the observed surface ECG is complex—the AP may vary across the heart, and the observed surface ECG results from the spatial/temporal derivative of the distribution of potentials and activation times. Nevertheless, a useful approximation, particularly for the V leads, is that the shape of the T-wave is controlled by the difference between the Endo- and Epicardium APs. Referring to FIG. 9, activation of the myocardium begins at the Purkinje fibers within the Endocardium 910 and propagates outwardly activating the Epicardium 920 last. The QRS complex 930 results from the timing differences in the activation across the myocardium and the T-wave is controlled by the difference in the repolarization segments of the APs.

Many studies have also documented that the Epicardium AP is most sensitive to ischemic change, and lab studies have strongly linked alternans with the onset of ischemia, while the Endocardium AP is relatively stable to ischemic changes (see Ionic Current Basis of Electrocardiographic waveforms, *K. Gima & Y. Rudy, Circulation Research, p. 889–896, 2002*, which is incorporated by reference). Thus, alternans most likely represent alternation of the Epicardium AP.

Still referring to FIG. 9, the earliest part of the AP is the depolarization phase 940 that exhibits a very abrupt onset and the key driver for the QRS complex. The following plateau 950 is the refractory period when the cardiac tissue is unable to respond to additional stimulus. Finally, the myocytes re-polarize 960 in preparation for the next cycle and the AP decays back to the starting potential. The T-wave reflects the re-polarization process and the peak of the T-wave corresponds to end of the Epicardium AP. The importance of this observation is that variability in AP morphology measured in lab specimens can be used as a guide for understanding the range of likely variability in the T-wave alternan signals. See "*Mechanism Linking T-wave Alternans to the Genesis of Cardiac Fibrillation,*" Pastore et al, *Circulation*, p. 1358, 1999, which is incorporated by reference. The following paragraphs highlight several observed variations in AP shape and the expected T-wave changes, and resulting alternan signals.

2. Pattern I—Variability in the Amplitude of Depolarization

Figure 10:
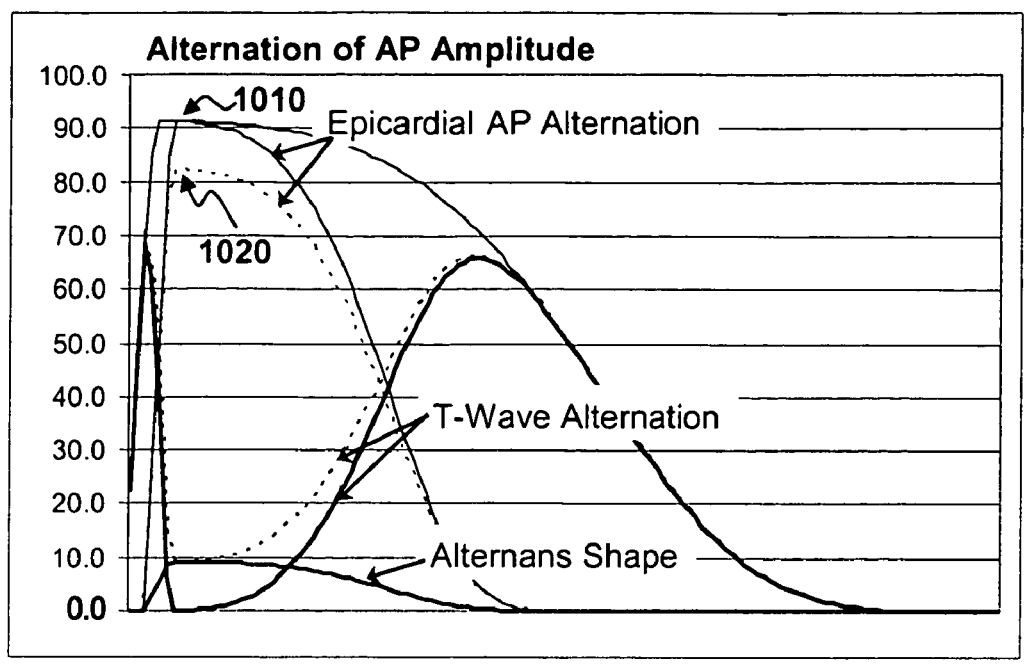
FIG. 10 is a graph illustrating an alternan signal associated with amplitude alternans in the depolarization phase of the epicardial AP in accordance with an embodiment of the invention.

One variation comes from changes in the strength or amplitude of the depolarization phase, while the refractory and re-polarization phases retain their characteristic shapes and time constants. FIG. 10 shows the AP, T-waves and alternan signal for this case, illustrating variations between a strong Epicardium AP 1010 and an amplitude diminished Epicardium AP 1020. The resulting T-wave variability will alternate with an amplitude scaling directly related to the variability of the Epicardium depolarization amplitude. Note that the polarity of the alternan signal, i.e., a maximum or a minimum, is dependent upon which beat—even or odd— contains the alternan signal.

This is the most simple example, but clearly links a possible alternan signal with alternating S-T segment elevation/depression, commonly associated with ischemia and myocardial infarcts, that has maximum amplitude at the end of the QRS complex—the S-T Junction—and tapers to zero at the apex of the T-wave. This model has an important auxiliary prediction: the alternation in depolarization amplitude should also cause an alternation in the QRS amplitude, which has rarely been observed with standard ECG recordings. However, the extremely high frequency content of the depolarization (~1000 Hz) is well above the band-pass of common ECG equipment.

3. Pattern II—Variability in the Refractory Period

Figure 11:
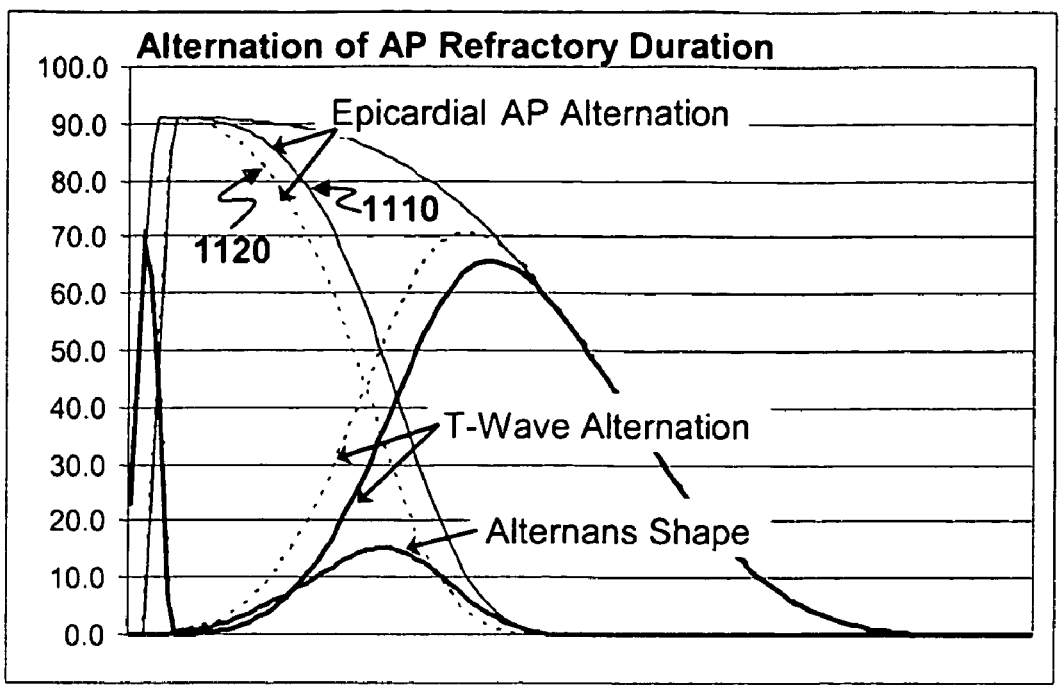
FIG. 11 is a graph illustrating an alternan signal associated with alternans in the epicardial refractory period of the AP in accordance with an embodiment of the invention.

This model assumes that the depolarization amplitude of the Epicardium and the time constants for re-polarization remain constant, but the plateau refractory period oscillates in an alternating pattern. FIG. 11 shows the associated APs, the T-waves and the alternating duration of the plateau from long 1110 to short 1120. For this model the alternan signal will peak around the mid-point between the end of the QRS complex and the maximum of the T-wave, tapering to zero at both ends.

4. Pattern III—Variability in the Repolarization Time Constant

Figure 12:
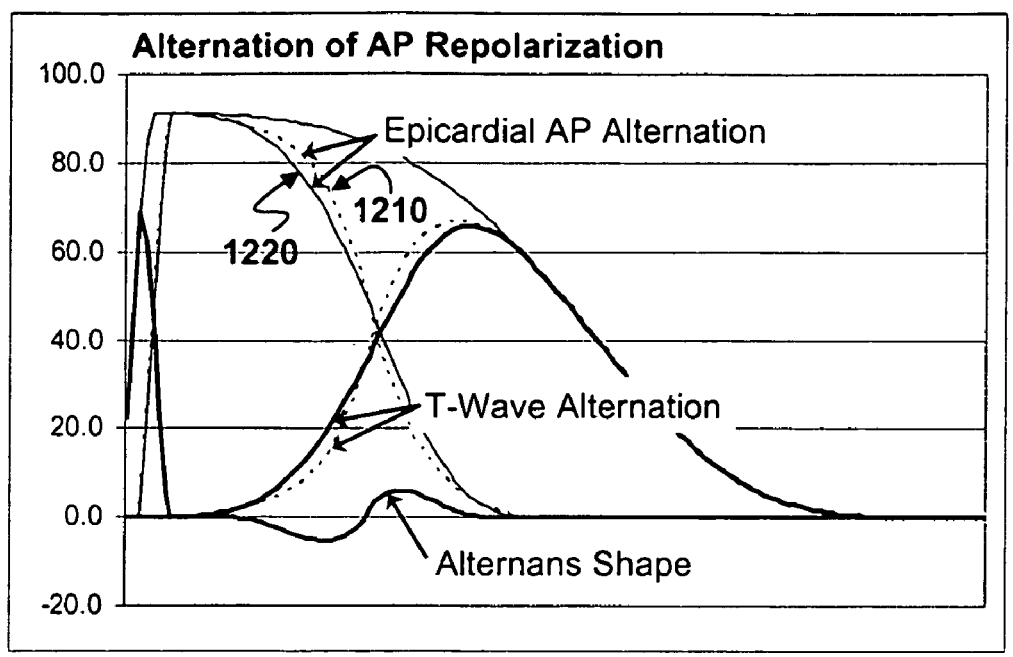
FIG. 12 is a graph illustrating an alternan signal associated with alternans in the epicardial repolarization phase the AP in accordance with an embodiment of the invention.

The third possibility is that the Epicardium repolarization time constant alternates between beats. FIG. 12 shows one possible variant in repolarization, with one phase exhibiting a rapid or steep repolarization 1210 and the other a more modest slope 1220, along with the change in the T-wave shape and the resulting predicted alternan signal. Note that this alternan shape is distinct from the previous two patterns, exhibiting a biphasic character and tapering to zero at the end of the QRS complex and the peak of the T-wave.

5. AP Variant Discussion

There are three key electrical activities that characterize the shape of the cardiac AP: a depolarization causing an abrupt rise in potential; a refractory plateau characterized by a slowly varying potential; and, a repolarization with the rapid decay of the potential and return of the heart to a state of excitability. Three possible AP variants have been investigated as models that capture the key observations reported in lab studies of measured APs.

The characteristic variations in each of the three phases of the cardiac AP are predicted to be associated with three very different alternan signatures. This suggests that the shape of the alternan curve may lead to a diagnostic method for identifying and focusing attention on specific cellular activities that are under duress in the stressed heart. Alternan methods of the prior art that just focus on the absolute average amplitude of the T-wave difference ignore most of the potential data contained in the alternating morphology. In addition, many AP studies have indicated that the stressed heart can disassociate from uniform alternan behavior to zones of tissue responding with different, or out-of-phase, alternans, leading to significant electrical instabilities that trigger re-entry and life threatening arrhythmias. Using the alternan morphology and polarity information derived from different surface electrodes in a standard 12 lead stress test offers a promise of identification of alternan disassociation and improved patient risk stratification.

It is important to note that the family of possible AP variability is large and the above discussion is not meant to represent the entire family of useful curves. Ongoing clinical studies will guide the refinement and selection of curves that represent typical observations. However, the general shape of the above three curves are sufficient to support early clinical studies.

6. Matching Model Curves and Data

Figure 13:
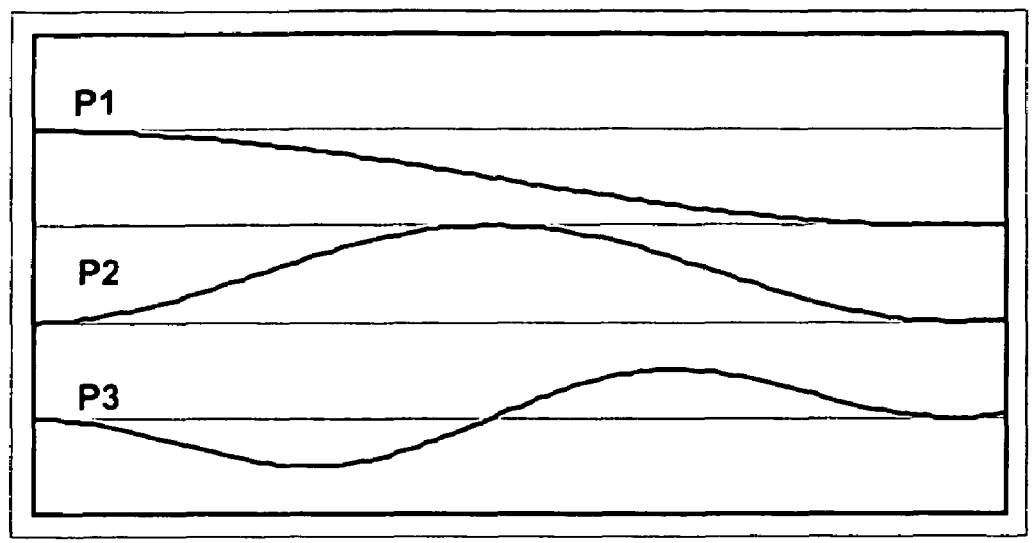
FIG. 13 is a diagram illustrating the parametric form of three curves used to decompose the alternan signature into the three phases of the associated AP in accordance with an embodiment of the invention.

The above discussed model curves are part of a family of orthogonal curves that can be fit to the best estimate of the alternan signal, An(i), defined above. The following parametric curves capture the morphology of the above discussed models and form a reasonable starting point:

$$P_1(i) = 0.5 \times \left[\operatorname{Cos}\left(\frac{\pi i}{l}\right) + 1\right]$$

$$P_2(i) = 0.5 \times \left[\operatorname{Sin}\left(\frac{2\pi i}{l} - \frac{\pi}{2}\right) + 1\right]$$

$$P_3(i) = 0.65 \times \operatorname{Sin}\left(\frac{\pi i}{l}\right) \times \operatorname{Sin}\left(\frac{-2\pi i}{l}\right)$$

where i is the sample number and l is the number of samples in the windowed T-wave between the start of the window and the peak of the T-wave. The curves should be padded with zeros between the peak of the T-wave and the end of the T-wave window. The curves have been normalized to a peak to peak amplitude of 1. The graphical form of these curves is shown in FIG. 13. After computing these three curves, each should be smoothed and sub-sampled using the same filter methods used above to smooth the alternan estimates.

The alternan signal can be decomposed into components representing the contribution from each of these distinct curves and AP processes. This is done by minimizing the least squares error between the model and the data by finding the optimal values for $A_n$ and C in the equation:

$$A_1 P_1(i) + A_2 P_2(i) + A_3 P_3(i) + C = An(i)$$

where each $A_n$ represents the amplitude of the corresponding model curve and C represents any residual DC bias in the alternan estimate. In a matrix notation this defines an over determined system of equations:

$$\begin{pmatrix} P_1(1) & P_2(1) & P_3(1) & 1 \\ P_1(2) & P_2(2) & P_3(2) & 1 \\ \ldots & \ldots & \ldots & \ldots \\ P_1(n) & P_2(n) & P_3(n) & 1 \end{pmatrix} \begin{pmatrix} A_1 \\ A_2 \\ A_3 \\ C \end{pmatrix} = \begin{pmatrix} An(1) \\ An(2) \\ \ldots \\ An(n) \end{pmatrix}$$

And the solution is:

$$\begin{pmatrix} A_1 \\ A_2 \\ A_3 \\ C \end{pmatrix} = \begin{pmatrix} \sum_n P_1^2(i) & \sum_n P_1(i)P_2(i) & \sum_n P_1(i)P_3(i) & \sum_n P_1(i) \\ \sum_n P_1(i)P_2(i) & \sum_n P_2^2(i) & \sum_n P_2(i)P_3(i) & \sum_n P_2(i) \\ \sum_n P_1(i)P_3(i) & \sum_n P_2(i)P_3(i) & \sum_n P_3^2(i) & \sum_n P_3(i) \\ \sum_n P_1(i) & \sum_n P_2(i) & \sum_n P_3(i) & n \end{pmatrix}^{-1}$$

$$\begin{pmatrix} \sum_n P_1(i)An(i) \\ \sum_n P_2(i)An(i) \\ \sum_n P_3(i)An(i) \\ \sum_n An(i) \end{pmatrix}$$

K. Model Standard Deviation

The weighted Standard Deviation should be computed from:

$$\text{S.D.} = \left[ \frac{1}{\sum_{j=1}^{m} \text{Weight}(j)} \sum_{j=1}^{m} \text{Weight}(j) \times \left( \frac{1}{n} \sum_{i=1}^{n} (A_1 P(i) + A_2 P(i) + A_3 P(i) + C - \text{Alt\_Smoothed}(i,j))^2 \right) \right]^{\frac{1}{2}}$$

for m estimates of the alternan signal at n values for each individual estimate. Weight(j) is defined above.

L. Reporting the Results

The above analysis will result in a very large amount of data. Good reporting metrics and tools for visualizing the results and efficiently communicating the clinical significance is considered important. The following sections describe these areas.

1. Onset of Alternans and Disassociation

Figure 14:
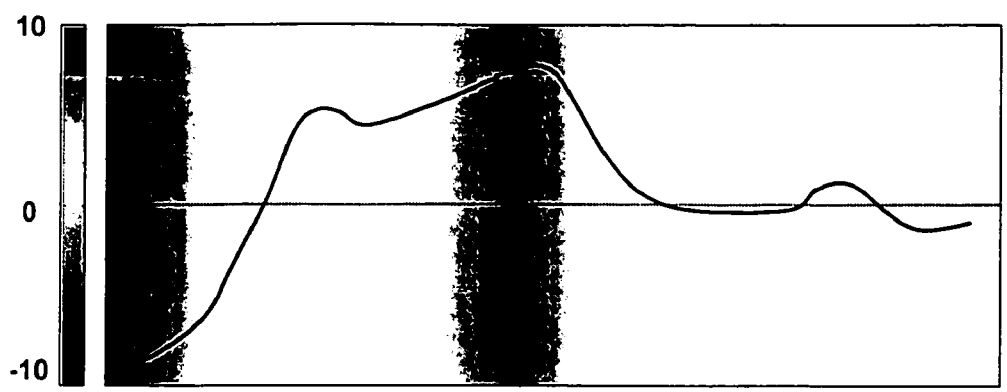
FIG. 14 is a graph illustrating an example of color coding corresponding to the amplitude of the alternan signature in accordance with an embodiment of the invention.
Figure 15:
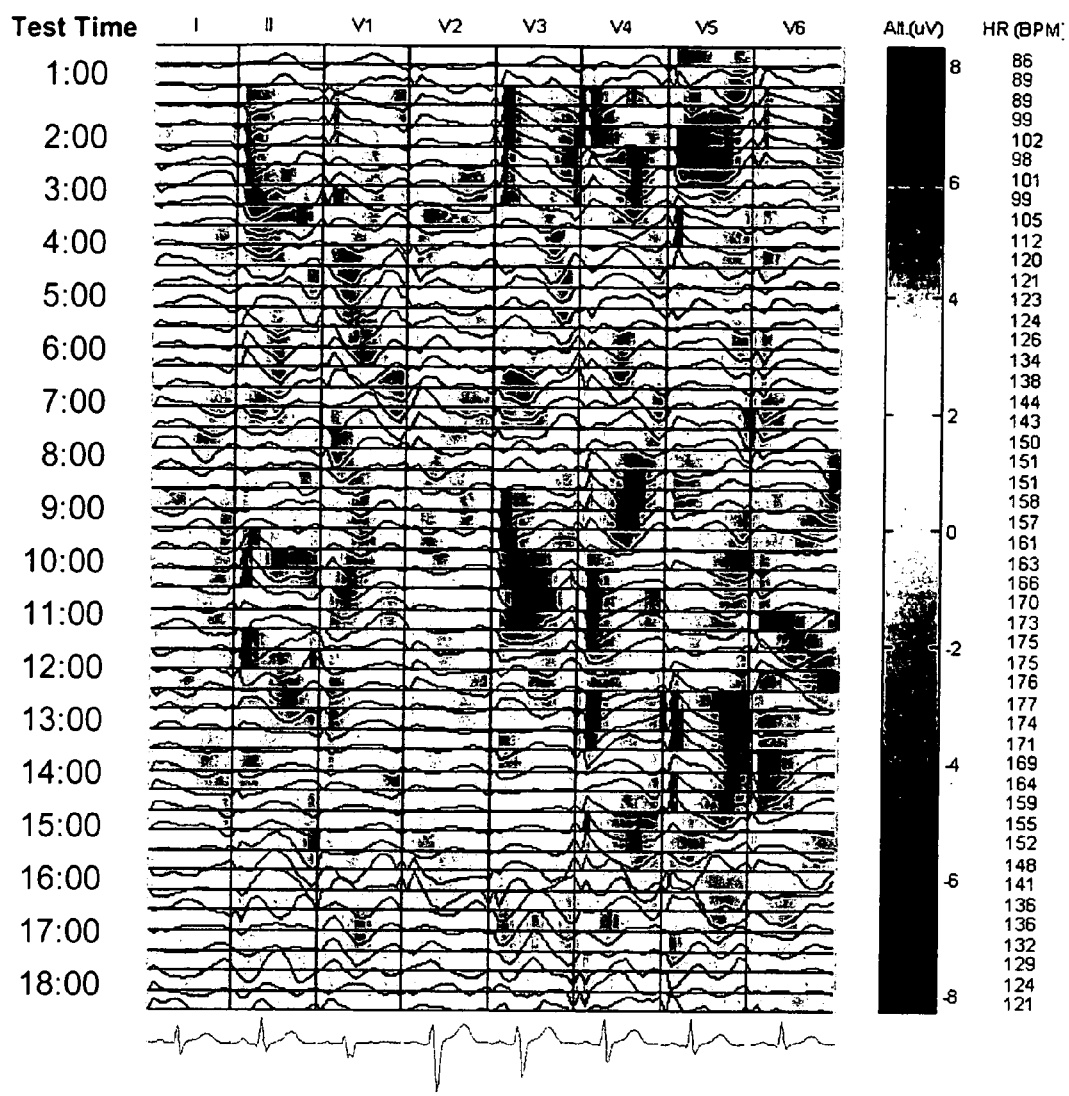
FIG. 15 is a representation of a composite display of the alternan signature for an entire stress test, including data for 8 independent ECG leads in accordance with an embodiment of the invention.

As best illustrated in FIG. 14, a color coding scheme of the display follows the amplitude curve for each individual estimate of the alternan signal. This permits easy visual assessment of amplitude in addition to convenient evaluation of the alternan signal signature. The complete test summary, for all leads, is developed by compositing together each individual alternan estimate as shown in FIG. 15. This is the most important summary graph that forms the basis for clinical analysis. It has been designed to clearly show the onset and amplitude of any statistically significant alternan signal and highlight alternan disassociation observed across the lead set, which should be visible as both changes in shape from lead to lead and changes in color (amplitude). Key elements of the display are:

Time Scale—Left Side: The test is graphically portrayed as a series of T-wave alternan estimates during the course of the stress test. In this example, the test was 18 minutes in length. T-wave alternan estimates are computed from a sliding window of individual alternan estimates.

Leads—Top: For a standard 12-lead test the results for the eight independent leads are shown. Leads III and the augmented leads could be added if clinical needs dictate—but the selected leads are expected to be sufficient for most applications. For higher lead tests, such as a 15-lead test, additional lead results may be added to the display.

Heart Rate—Right Side: The computed heart rate at intervals during the test are shown. The heart rates are associated with the displayed estimates of the alternan signal.

Alternans: The curves shown on each lead panel are the smoothed alternan estimate An(i) correctly placed vertically with regard to the test time and heart rate.

Color: The color spectrum scale may be either dynamically scaled for the range of the alternan values, or fixed to a constant color scale to facilitate comparisons between different subjects. The spectrum should be 32–64 colors deep. Color coding may be set to white or no-fill if the Standard Deviation estimate for the alternan is greater than the maximum amplitude (Amp) associated with the smoothed alternan estimate An(i).

Average Beats: The resting average beats may be shown at the bottom of each lead column. It may also be useful to display the average beats corresponding to the maximum heart rate or maximum alternan signal.

2. Alternan Disassociation Index

Clinical studies have shown that alternans can disassociate or become out of phase across the heart (i.e., one zone may exhibit a high-low or odd-even pattern while the adjacent zone is exhibiting a low-high or even-odd pattern). This reflects out-of-phase Epicardium AP augmentations and diminutions across small spatial zones (see, for example, "Mechanism Linking T-wave Alternans to the Genesis of Cardiac Fibrillation," Pastore et al, Circulation, p. 1358, 1999, which is incorporated by reference), creating significant electrical gradients and potentially triggering re-entry and arrhythmia. The alternan induced electric gradient is controlled by the voltage differences of the alternan signals, as recorded by each lead, and the spatial separation on the heart associated with the region of the heart sampled by each lead. This leads to a metric or index for judging the severity of disassociation useful in risk stratification:

$$ADI = \text{Max}\left\{\text{Abs}\left[\frac{(An(i, j, T) - An(i, k, T))}{(j-k)}\right]\right\} \quad j \neq k$$

where j and k represent the V lead index, from 1–6 for a standard 12-lead test, for An(i) at time T in the test. This expression can be generalized for higher lead tests.

3. Alternan Amplitude and Heart Rate Trending

Figure 16:
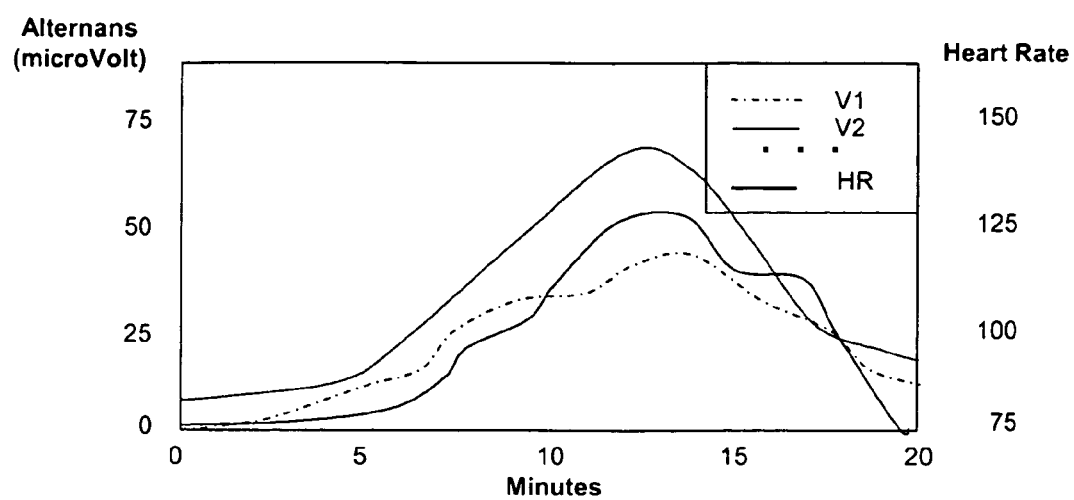
FIG. 16 is a graph showing a possible display of average alternan amplitude and heart rate for a stress test in accordance with an embodiment of the invention.

FIG. 16 presents selected data regarding the averaged alternan signal for a given time period during the stress test. The horizontal axis represents the stress test duration. The left axis is the alternan amplitude and the right axis is the heart rate. Preferably, the alternan data for each desired lead is plotted as shown.

We claim:

1. A method of reporting T-wave alternan values, comprising:
   obtaining T-wave alternan values corresponding to alternans at common respective time intervals of a plurality of T-wave segments obtained from a physiological signal representative of a patient's heartbeat by differencing adjacent T-wave segments such that polarity and morphology information from the physiological signal are retained in the T-wave alternan values; and
   displaying a representation of a plurality of the T-wave alternan values at the common respective time intervals of the T-wave segments.

2. The method of claim 1 wherein displaying a representation of the T-wave alternan values comprises generating a graphic display related to the amplitude of the T-wave alternan values at the common respective time intervals for selected heart rates.

3. The method of claim 2 wherein generating a graphic display related to the amplitude of the T-wave alternan values at the common respective time intervals comprises generating a plot of the T-wave alternan values versus T-wave segment time.

4. The method of claim 2 wherein generating a graphic display related to the amplitude of the T-wave alternan values at the common respective time intervals comprises color coding relative amplitudes of T-wave alternan values and displaying colors corresponding to the relative amplitudes of the T-wave alternan values at the common respective time intervals.

5. The method of claim 4 wherein white is assigned to a T-wave alternan value having an amplitude less than a standard deviation for the T-wave alternan values.

6. The method of claim 2 wherein generating a graphic display related to the amplitude of the T-wave alternan values at the common respective time intervals comprises (a) generating a plot of the T-wave alternan values versus T-wave segment time and (b) color coding relative amplitudes of T-wave alternan values and displaying colors corresponding to the relative amplitudes of the T-wave alternan values at the common respective time intervals.

7. The method of claim 6 wherein white is assigned to a T-wave alternan value having an amplitude less than a standard deviation for the T-wave alternan values.

8. The method of claim 1, further comprising displaying a plot of a waveform indicative of a heartbeat associated with the T-wave alternan values.

9. The method of claim 1 wherein the physiological signal is from a lead and displaying a representation of a plurality of the T-wave alternan values comprises providing a plurality of time periods of a stress test, and wherein each time period has a graphical representation of the T-wave alternan values for a plurality of T-wave segments.

10. A method of reporting T-wave alternan values, comprising:
    obtaining T-wave alternan values corresponding to alternans at common respective time intervals of a plurality of T-wave segments obtained from a physiological signal representative of a patient's heartbeat, the physiological signal being measured by a plurality of leads, and the T-wave alternan values beinG obtained by differencing adiacent T-wave segments such that polarity and morphology information from the physiological signal are retained in the T-ware alternan values; and
    displaying a representation of a plurality of the T-wave alternan values at the common respective time intervals of the T-wave segments.

11. The method of claim 10 wherein displaying a representation of the T-wave alternan values comprises providing a plurality of time periods of a stress test for each lead, and wherein each time period has a graphical representation of the T-wave alternan values for a plurality of T-wave segments.

12. The method of claim 11 wherein displaying a representation of the T-wave alternan values further comprises generating a graphic display related to the amplitude of the T-wave alternan values at the common respective time intervals for selected heart rates.

13. The method of claim 12 wherein generating a graphic display related to the amplitude of the T-wave alternan values at the common respective time intervals comprises generating a plot of the T-wave alternan values versus T-wave segment time.

14. The method of claim 12 wherein generating a graphic display related to the amplitude of the T-wave alternan values at the common respective time intervals comprises color coding relative amplitudes of T-wave alternan values and displaying colors corresponding to the relative amplitudes of the T-wave alternan values at the common respective time intervals.

15. The method of claim 14 wherein white is assigned to a T-wave alternan value having an amplitude less than a standard deviation for the T-wave alternan values.

16. The method of claim 12 wherein generating a graphic display related to the amplitude of the T-wave alternan values at the common respective time intervals comprises (a) generating a plot of the T-wave alternan values versus T-wave segment time and (b) color coding relative amplitudes of T-wave alternan values and displaying colors corresponding to the relative amplitudes of the T-wave alternan values at the common respective time intervals.

17. The method of claim 16 wherein white is assigned to a T-wave alternan value having an amplitude less than a standard deviation for the T-wave alternan values.

18. The method of claim 10, further comprising displaying a plot of a waveform indicative of a heartbeat associated with the T-wave alternan values.

19. A method of reporting T-wave alternan values, comprising:
   identifying T-wave segments of a physiological signal having substantially repeating waveforms representative of a patient's heartbeat;
   computing differences at common respective time intervals of selected T-wave segments to provide preliminary alternan estimates by differencing adjacent T-wave segments such that polarity and morphology information from the physiological signal are retained in the T-wave alternan values;
   ascertaining median estimates of alternans over periods containing a plurality of heartbeats from the preliminary alternan estimates;
   determining a final alternan waveform based on smoothed alternan estimates derived from the preliminary alternan estimates by weighting the smoothed alternan estimates based on the median estimates of alternans, the final alternan waveform defining T-wave alternan values corresponding to alternans at common respective time intervals in the T-wave segments; and
   displaying a representation of a plurality of the T-wave alternan values at the common respective time intervals of the T-wave segments.

20. The method of claim 19 wherein displaying a representation of the T-wave alternan values comprises generating a graphic display related to the amplitude of the T-wave alternan values at the common respective time intervals for selected heart rates.

21. The method of claim 20 wherein generating a graphic display related to the amplitude of the T-wave alternan values at the common respective time intervals comprises generating a plot of the T-wave alternan values versus T-wave segment time.

22. The method of claim 20 wherein generating a graphic display related to the amplitude of the T-wave alternan values at the common respective time intervals comprises color coding relative amplitudes of T-wave alternan values and displaying colors corresponding to the relative amplitudes of the T-wave alternan values at the common respective time intervals.

23. The method of claim 22 wherein white is assigned to a T-wave alternan value having an amplitude less than a standard deviation for the T-wave alternan values.

24. The method of claim 20 wherein generating a graphic display related to the amplitude of the T-wave alternan values at the common respective time intervals comprises (a) generating a plot of the T-wave alternan values versus T-wave segment time and (b) color coding relative amplitudes of T-wave alternan values and displaying colors corresponding to the relative amplitudes of the T-wave alternan values at the common respective time intervals.

25. The method of claim 24 wherein white is assigned to a T-wave alternan value having an amplitude less than a standard deviation for the T-wave alternan values.

26. The method of claim 19, further comprising displaying a plot of a waveform indicative of a heartbeat associated with the T-wave alternan values.

27. The method of claim 19 wherein the physiological signal is from a lead and displaying a representation of a plurality of the T-wave alternan values comprises providing a plurality of time periods of a stress test, and wherein each time period has a graphical representation of the T-wave alternan values for a plurality of T-wave segments.

* * * * *

UNITED STATES PATENT AND TRADEMARK OFFICE
CERTIFICATE OF CORRECTION

PATENT NO. : 7,136,694 B2  
APPLICATION NO. : 10/815290  
DATED : November 14, 2006  
INVENTOR(S) : Hadley et al.

It is certified that error appears in the above-identified patent and that said Letters Patent is hereby corrected as shown below:

On the face page, in field (56), under "U.S. Patent Documents", in column 2, line 11, delete "B1" and insert -- B2 --, therefor.

On Sheet 19 of 20, in Fig. 15, line 1, delete "(BMP:" and insert -- (BMP) --, therefor.

In column 10, line 16, after "trace" insert -- . --.

In column 11, line 56, delete "Nyquest" and insert -- Nyquist --, therefor.

In column 17, line 62, delete "P3" and insert -- $P_3$ --, therefor.

In column 20, line 41, in Claim 10, delete "beinG" and insert -- being --, therefor.

In column 20, line 42, in Claim 10, delete "adiacent" and insert -- adjacent --, therefor.

In column 21, line 28, in Claim 19, delete "adiacent" and insert -- adjacent --, therefor.

Signed and Sealed this

Twenty-third Day of December, 2008

JON W. DUDAS  
*Director of the United States Patent and Trademark Office*